(12) United States Patent
Scherich et al.

(10) Patent No.: US 11,992,644 B2
(45) Date of Patent: May 28, 2024

(54) FLUSH INSTRUMENT WITH BLOOD EXPOSURE PROTECTION AND RELATED METHODS

(71) Applicant: Becton, Dickinson and Company, Franklin Lakes, NJ (US)

(72) Inventors: Megan Scherich, Salt Lake City, UT (US); Curtis H. Blanchard, Riverton, UT (US); Yiping Ma, Layton, UT (US); Weston F. Harding, Lehi, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 591 days.

(21) Appl. No.: 17/127,588

(22) Filed: Dec. 18, 2020

(65) Prior Publication Data

US 2021/0213268 A1 Jul. 15, 2021

Related U.S. Application Data

(60) Provisional application No. 62/959,050, filed on Jan. 9, 2020.

(51) Int. Cl.
*A61M 39/02* (2006.01)
*A61M 25/09* (2006.01)

(52) U.S. Cl.
CPC .. *A61M 39/0247* (2013.01); *A61M 25/09041* (2013.01); *A61M 2039/0202* (2013.01); *A61M 2039/0205* (2013.01); *A61M 2039/0258* (2013.01); *A61M 2039/0291* (2013.01)

(58) Field of Classification Search
CPC ........ A61M 39/0247; A61M 25/09041; A61M 2039/0202; A61M 2039/0205; A61M 2039/0258; A61M 2039/0291
See application file for complete search history.

(56) References Cited

U.S. PATENT DOCUMENTS

| 5,730,150 A | * | 3/1998 | Peppel | A61M 25/09041 |
| | | | | 600/585 |
| 9,861,792 B2 | * | 1/2018 | Hall | A61M 25/09 |
| 2012/0197200 A1 | * | 8/2012 | Belson | A61M 25/065 |
| | | | | 604/164.12 |
| 2014/0180250 A1 | * | 6/2014 | Belson | A61M 25/0606 |
| | | | | 604/510 |

(Continued)

FOREIGN PATENT DOCUMENTS

WO 2018/213148 11/2018

*Primary Examiner* — Nathan R Price
*Assistant Examiner* — Mark A Igel
(74) *Attorney, Agent, or Firm* — The Webb Law Firm

(57) ABSTRACT

A system for accessing a patient's vascular system may have a tube with a wall that defines an exterior surface and lumen with a proximal end and a distal end, and a guidewire that is deployable, by sliding distally, from a retracted position in which the guidewire resides in the lumen, to a deployed position in which the guidewire extends beyond the distal end. The system may further have a retraction mechanism that can be actuated to retract the guidewire from the deployed position to the retracted position, or a protective shield that can be actuated to extend distally from the distal end of the tube to cover the guidewire in the deployed position.

19 Claims, 25 Drawing Sheets

(56) References Cited

U.S. PATENT DOCUMENTS

| | | | | |
|---|---|---|---|---|
| 2014/0364809 A1* | 12/2014 | Isaacson | ........... | A61M 25/0097 |
| | | | | 604/164.08 |
| 2017/0209668 A1* | 7/2017 | Belson | ............ | A61M 25/09041 |
| 2019/0321595 A1* | 10/2019 | Spataro | ............. | A61M 25/0662 |

* cited by examiner

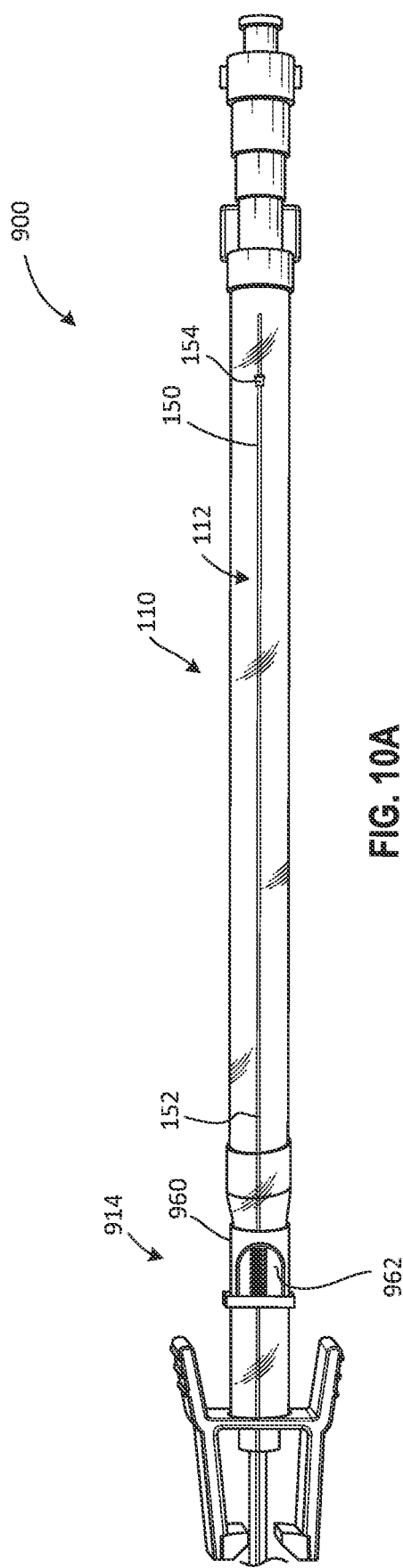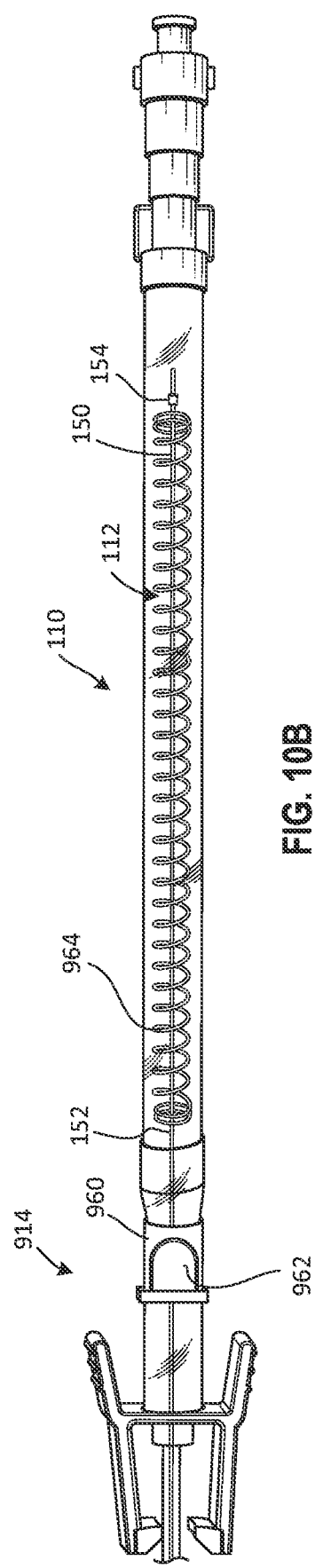
FIG. 10A
FIG. 10B

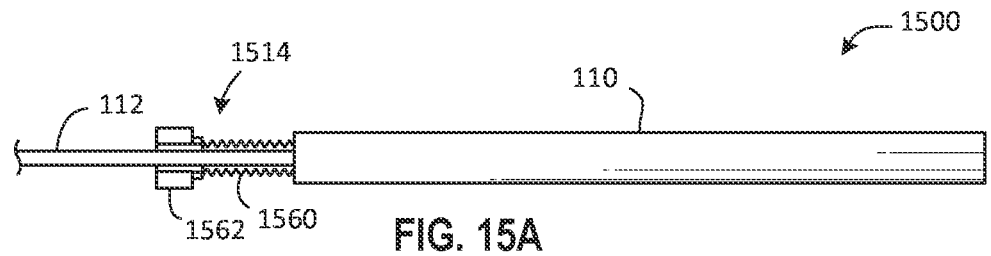
FIG. 15A
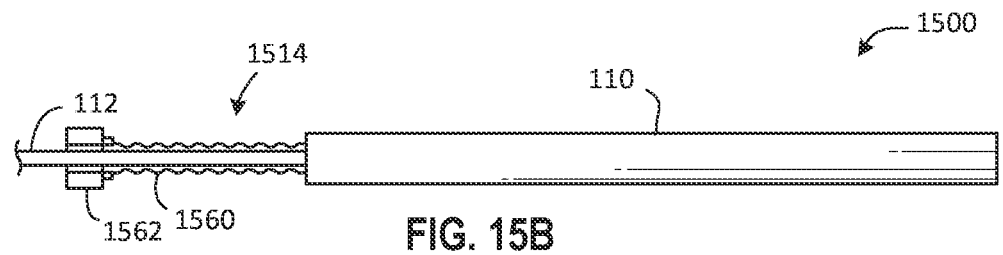
FIG. 15B
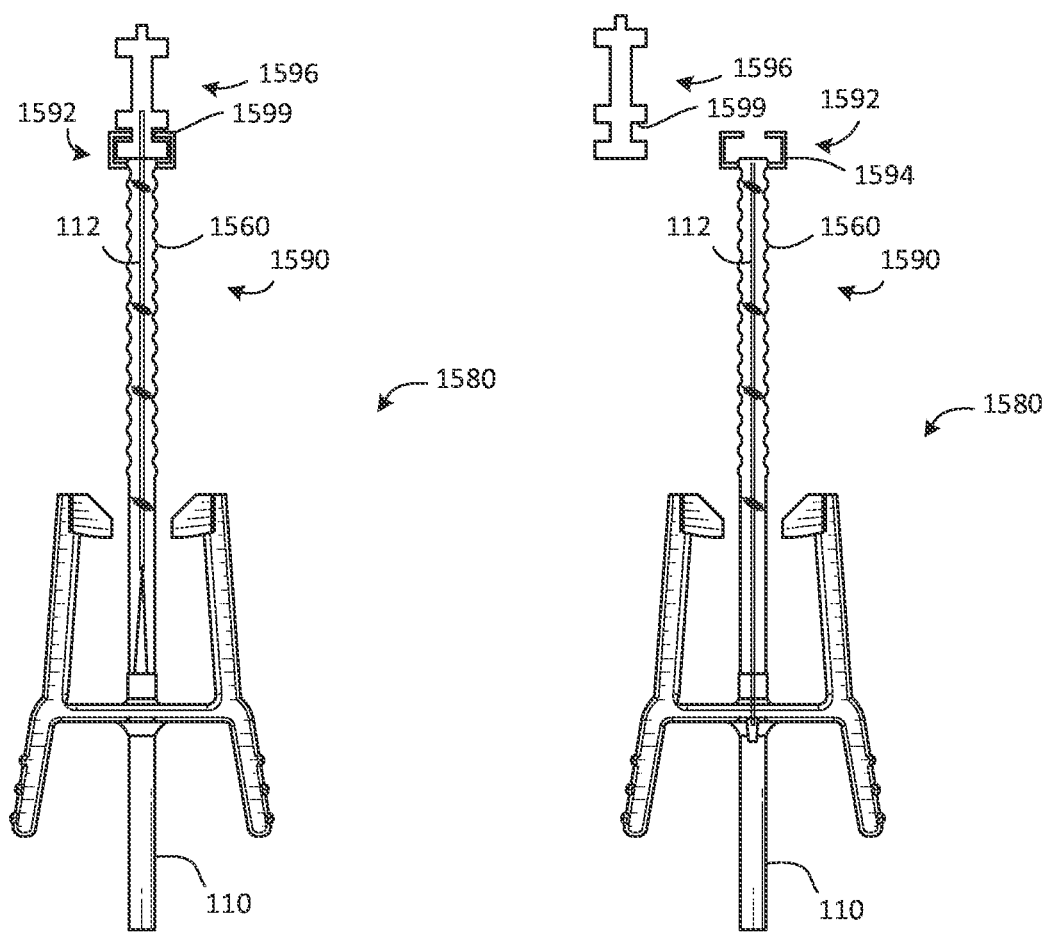
FIG. 15C
FIG. 15D

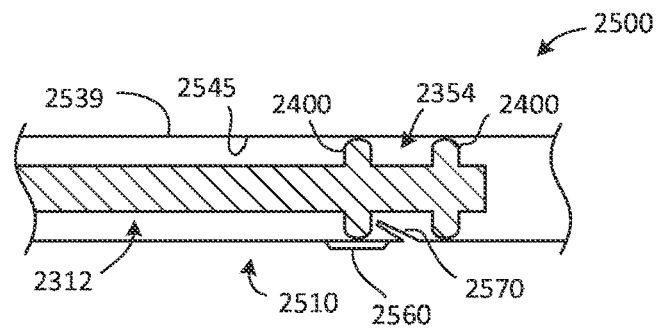
FIG. 25A
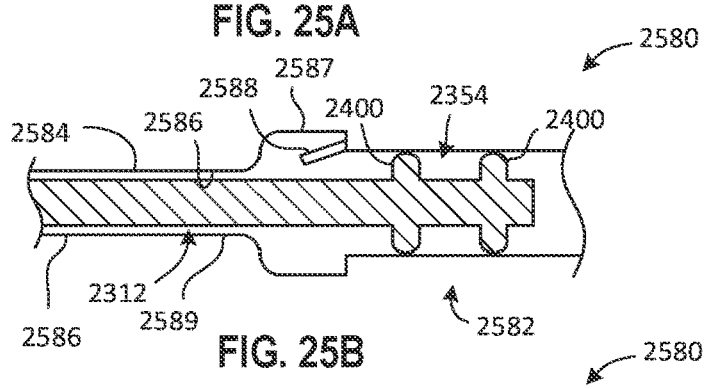
FIG. 25B
FIG. 25C
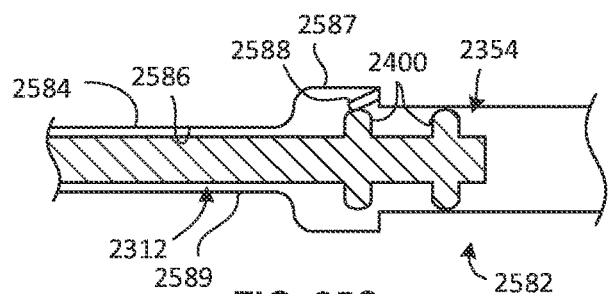
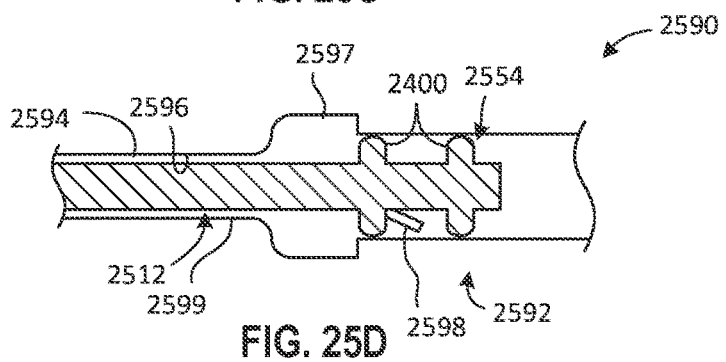
FIG. 25D
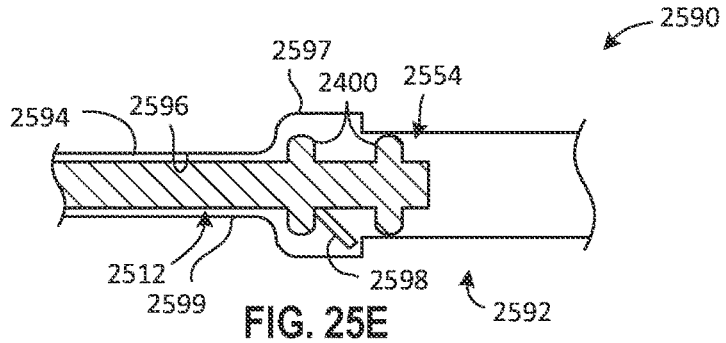
FIG. 25E

US 11,992,644 B2

FLUSH INSTRUMENT WITH BLOOD EXPOSURE PROTECTION AND RELATED METHODS

RELATED APPLICATIONS

This application claims the benefit of U.S. Provisional Application No. 62/959,050, filed Jan. 9, 2020, and entitled FLUSH INSTRUMENT WITH BLOOD EXPOSURE PROTECTION AND RELATED METHODS, which is incorporated herein in its entirety.

BACKGROUND

Many different vascular access devices (VAD's) are used to provide access to a patient's vascular system, for example, to infuse blood, aspirate blood, deliver medication, deliver nutrients, or monitor the condition of a patient's blood. In many instances, it is desirable to perform more than one of these functions, either sequentially or simultaneously, for a given patient. Many VAD's include a catheter line that is connected to a patient's vein via a cannula. Unfortunately, with many existing systems, this entails the connection of a new VAD, leading to another needle insertion for the patient.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a system for accessing a patient's vascular system. In some embodiments, a vascular access instrument delivery device may provide needle-free delivery of a probe to a patient's vascular system for blood collection, fluid delivery, patient or device monitoring, or other clinical needs by utilizing an existing vascular access device (VAD) to reduce trauma to the vein and overcome obstructions such as thrombus, valves, and/or a fibrin sheath in or around the VAD or vein that may otherwise prevent blood draw.

In some embodiments, the system may have a tube with a wall that defines an exterior surface and lumen with a proximal end and a distal end, and a guidewire that is deployable, by sliding distally, from a retracted position in which the guidewire resides in the lumen, to a deployed position in which the guidewire extends beyond the distal end. In some embodiments, the system may have a retraction mechanism that can be used to retract the guidewire from the deployed position to the retracted position, or a protective shield that can be used to extend distally from the distal end of the tube to cover the guidewire in the deployed position.

In some embodiments, the proximal end may be connectable to a source of pressurized fluid. In some embodiments, the guidewire may be deployable in response to pressure, proximal to the lumen, from the source of pressurized fluid. In some embodiments, the system may have an extension set for the VAD. In some embodiments, the distal end may have a blunt cannula configured to mate with a needleless access connector of the VAD. In some embodiments, the system may include a cap configured to cover the blunt cannula prior to attachment of the blunt cannula to the VAD.

In some embodiments, the system may include the retraction mechanism, which may be slidably coupled to the exterior surface. In some embodiments, the retraction mechanism may be coupled to the guidewire such that motion of the retraction mechanism toward the proximal end retracts the guidewire from the deployed position to the retracted position. In some embodiments, the guidewire may have a distal portion with an elongated shape, and a proximal portion with a coupling feature. In some embodiments, the coupling feature may include a cross-sectional shape that is enlarged relative to the distal portion. In some embodiments, the retraction mechanism may be coupled to the coupling feature through the wall.

In some embodiments, the coupling feature may include one or more of the following: a wedge shape, one or more rounded ridges, one or more fins, one or more splines, one or more longitudinal ribs, and one or more anti-rotation features. In some embodiments, the retraction mechanism may compress the wall into contact with the coupling feature to cause the wall to urge the coupling feature to move proximally in response to proximal motion of the retraction mechanism.

In some embodiments, the retraction mechanism may include one or more of the following: one or more wheels that engage the exterior surface to compress the tube, one or more ball bearings that engage the exterior surface to compress the tube, and one or more manually compressible walls that can be flexed toward the tube. In some embodiments, the retraction mechanism may include one or more of the following: one or more magnets that magnetically engage the coupling feature, one or more springs coupled to the coupling feature, and a tether secured to the coupling feature.

In some embodiments, the system may include a spring that urges the guidewire to deploy from the retracted position to the deployed position. In some embodiments, the system may include the protective shield. In some embodiments, the system may include an absorbent component positioned to remove blood from the guidewire after deployment of the guidewire.

In some embodiments, the guidewire may include a spring with a variable pitch, and/or a secondary tube including an interior bore through which blood can be aspirated from the vascular system. In some embodiments, the proximal end may be connectable to a source of pressurized fluid. In some embodiments, the guidewire may be deployable in response to pressure, proximal to the lumen, from the source of pressurized fluid. In some embodiments, the guidewire may be the secondary tube. In some embodiments, the guidewire may have a valve that is closed during deployment of the guidewire and open during aspiration of blood from the vascular system. In some embodiments, at least one of the guidewire and the tube may have a catch mechanism that retains the guidewire in the deployed position.

In some embodiments, a method for accessing a patient's vascular system may include positioning a tube proximate the vascular system. In some embodiments, the tube may have an exterior surface and lumen with a proximal end and a distal end. In some embodiments, the method may include deploying a guidewire by sliding the guidewire distally, from a retracted position in which the guidewire resides in the lumen, to a deployed position in which the guidewire extends beyond the distal end. In some embodiments, the method may include performing one or more of the following steps: retracting the guidewire from the deployed position to the retracted position by sliding a retraction mechanism, slidably coupled to the exterior surface, proximally, and extending a protective shield to extend distally from the distal end of the tube to cover the guidewire in the deployed position.

In some embodiments, the method may include prior to deploying the guidewire, moving the retraction mechanism to a predetermined position such that, during deployment of the guidewire, the retraction mechanism limits a range of proximal motion of the guidewire. In some embodiments, the method may include, with an absorbent component, removing blood from the guidewire after deployment of the guidewire. In some embodiments, the method may include, prior to deploying the guidewire, connecting the proximal end to a source of pressurized fluid.

In some embodiments, the guidewire may include a secondary tube with an interior bore and a valve. In some embodiments, deploying the guidewire may include, with the valve closed to prevent fluid flow through the interior bore, deploying the guidewire in response to pressure, proximal to the lumen, from the source of pressurized fluid. In some embodiments, the method may include, after deploying the guidewire, opening the valve to permit fluid flow through the interior bore, and aspirating blood through the interior bore.

According to some embodiments, a system for accessing a patient's vascular system may include a tube with a wall that defines an exterior surface and lumen with a proximal end and a distal end, and a guidewire that is deployable by sliding distally from a retracted position in which the guidewire resides in the lumen, to a deployed position in which the guidewire extends beyond the distal end. In some embodiments, the guidewire may have a distal portion with an elongated shape, and a proximal portion with a coupling feature with a cross-sectional shape that is enlarged relative to the distal portion. In some embodiments, the system may include a retraction mechanism that can be actuated to retract the guidewire from the deployed position to the retracted position. In some embodiments, the proximal end may be connectable to a source of pressurized fluid. In some embodiments, the guidewire may be deployable in response to pressure, proximal to the lumen, from the source of pressurized fluid. In some embodiments, the system may be an extension set for a VAD. In some embodiments, the distal end may have a blunt cannula configured to mate with a needleless access connector of the VAD.

The object and advantages of the embodiments will be realized and achieved at least by the elements, features, and combinations particularly pointed out in the claims. It is to be understood that both the foregoing general description and the following detailed description are exemplary and explanatory and are not restrictive of the invention, as claimed.

BRIEF DESCRIPTION OF THE SEVERAL VIEWS OF THE DRAWINGS

Example embodiments will be described and explained with additional specificity and detail through the use of the accompanying drawings in which:

FIGS. 10A and 10B are front elevation views of the system of FIG. 9, prior to deployment and after retraction, respectively, according to some embodiments.

FIGS. 15A, 15B are front elevation, schematic views of a system for accessing a patient's vascular system, in the deployed and retracted positions, respectively, according to some embodiments.

FIGS. 15C and 15D are front elevation views of the distal end of a system for accessing a patient's vascular system, in the retracted configuration, with a protective shield attached to and detached from a VAD, respectively, according to some embodiments.

FIG. 25A is a front elevation, section view of the proximal portion of a system for accessing a patient's vascular system, according to some embodiments.

FIGS. 25B and 25C are front elevation, section views of the proximal portion of a system for accessing a patient's vascular system, with the guidewire in unlocked and locked positions, respectively, according to some embodiments.

FIGS. 25D and 25E are front elevation, section views of the proximal portion of a system for accessing a patient's vascular system, with the guidewire in unlocked and locked positions, respectively, according to some embodiments.

DESCRIPTION OF EMBODIMENTS

Figure 1:
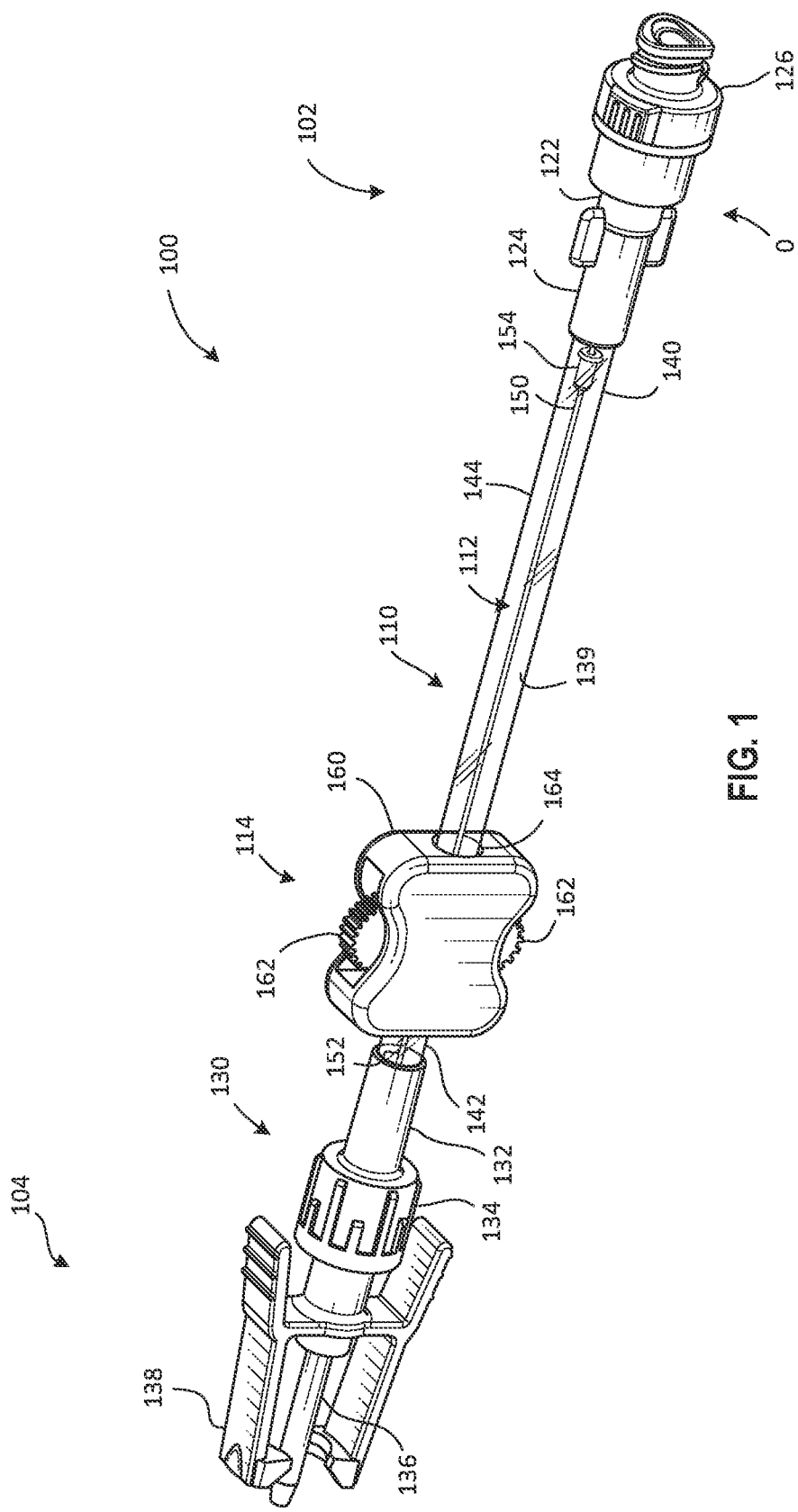
FIG. 1 is perspective view of a system for accessing a patient's vascular system, according to some embodiments.

Referring now to FIG. 1, FIG. 1 is perspective view of a system 100 for accessing a patient's vascular system, according to some embodiments. In some embodiments, the system 100 may have a proximal end 102 and a distal end 104. In some embodiments, the system 100 may further have a tube 110, a guidewire 112 housed within the tube 110 such that the guidewire 112 can be deployed distally from the tube 110, and a retraction mechanism 114 that facilitates withdrawal of the guidewire 112 distally back into the tube 110.

In some embodiments, the system 100 may include an extension set for a vascular access device (VAD—not illustrated), and may be designed to function in concert with the VAD to enable one or more actions to be performed in the patient's vascular system, while utilizing the access already provided by the VAD. Such actions may include, but are not limited to, monitoring the vascular system, aspirating blood or other fluids, infusing blood or other fluids into the vascular system, and/or the like. In some embodiments, the guidewire 112 may be deployed into the vascular system through existing VAD components, such as catheter and cannula that has already been placed in a patient's vein (not illustrated) to provide access to the patient's vascular system through the vein.

Thus, in some embodiments, the system 100 may be placed in-line with other VAD components. In some embodiments, the proximal end 102 and the distal end 104 may have features that facilitate such in-line connection. More specifically, the proximal end 102 may have a Luer connector 120, with a male component 122 and a female component 124, that connects the proximal end 102 to the tube 110. In some embodiments, the proximal end 102 may also have a proximal connector 126 that is connectable to a source of pressurized fluid, such as a syringe filled with saline solution, or the like. In some embodiments, the proximal connector 126 may optionally be permanently secured to the male component 122, for example, via bonding, an adhesive, RF welding, and/or the like to prevent accidental or intentional removal by the user.

Similarly, in some embodiments, the distal end 104 may have a Luer connector 130, with a male component 132 and a female component 134, that connects the distal end 104 to the tube 110. In some embodiments, the distal end 104 may also have a distal connector 136 designed to interface with the existing VAD. In some embodiments, the distal connector 136 may be a blunt cannula that fits within an existing female receiver in the VAD, or the like. In some embodiments, the distal connector 136 may optionally be permanently secured to the female component 134, for example, via bonding, an adhesive, RF welding, and/or the like, to prevent accidental or intentional removal by the user.

In some embodiments, the distal end 104 may further have a clip 138 that keeps the distal end 104 coupled to the VAD until the user desires to remove it. In some embodiments, the clip 138 is optional; in other embodiments, another Luer connection, or a persistent connection of a different type, may be used. Similarly, in other embodiments, the proximal connector 126 may be replaced with various alternatives and/or augmented with a clip or other retention device, if desired.

Although the embodiments disclosed herein generally utilize the distal connector 136 in the form of a blunt cannula, and the clip, all of these solutions may also be applied to a male Luer potentially with a rotary or fixed locking mechanism. They may also be applied to a Luer like male connector without the rotary locking mechanism but with a clip, such as the clip 138.

In some embodiments, the tube 110 may have a wall 139 that defines a proximal end 140, a distal end 142 and an exterior surface 144. In some embodiments, the guidewire 112 may be deployable through the VAD and into the patient's vascular system. In some embodiments, deployment may entail sliding the guidewire 112 distally so that the guidewire 112 slides from a retracted position, in which the guidewire 112 is contained entirely within the tube 110, to a deployed position, in which the guidewire 112 protrudes distally beyond the distal end 142 of the tube 110 and into the patient's vascular system through the VAD.

In some embodiments, the guidewire 112 may have a proximal end 150 and a distal end 152. In some embodiments, in the retracted configuration, the proximal end 150 of the guidewire 112 may reside within the proximal end 140 of the tube 110, and the distal end 152 of the guidewire 112 may reside within the distal end 142 of the tube 110. In some embodiments, the male component 122 may have a generally flexible configuration that enables the guidewire 112 to curve around bends in the tube 110, the VAD, and/or the patient's vascular system. Thus, in some embodiments, the guidewire 112 may be generally constructed as a wire, a spring, a combination of a wire and a spring, and/or the like. In some alternative embodiments, which will be described subsequently, aspiration may be carried out through a guidewire. In such embodiments, the guidewire may optionally be constructed as a tube through which aspiration can be carried out. Alternatively, aspiration may be carried out around the guidewire 112, through the tube 110. A device such as an LLAD and vacutainer or syringe may be used to accomplish the aspiration.

In some embodiments, the system 100 may be flushed in with a high viscosity fluid to increase drag between the fluid and tube 110 or guidewire 112 to facilitate deployment. In some embodiments, the guidewire may optionally have varying pitch along its length. For example, the pitch of the guidewire 112 upstream of the catheter tip may allow more blood flow, providing an increased flow rate. In some embodiments, the guidewire 112 may have a smaller pitch near the tip of the catheter to prevent blood clots from entering the device, but still allow blood flow through it. In some embodiments, the guidewire may or may not have a wire through the center for added stiffness to ease insertion.

Alternatively or additionally, in some embodiments, the guidewire 112 may have soft or stiff tubing that is flushed into the VAD instead of a spring or wire. In some embodiments, the soft or stiff tubing may be colored to increase visibility. In some embodiments, the soft or stiff tubing may serve to create a closed path for blood flow and prevent contamination of the blood due to drug adsorption in the VAD. In some embodiments, the inner diameter and length of the soft or stiff tubing may optionally be optimized to minimize shear of the red blood cells and therefore reduce hemolysis.

In some embodiments, a fluid pathway that extends through the system 100 may be optimized to reduce or minimize maximum shear stress during blood draw to reduce hemolysis. In some embodiments, a length of the fluid pathway may be selected based on one or more of the following: a gauge of a particular catheter, a particular VAD configuration, or a clinical setup. In some embodiments, the fluid pathway may include a length L from the proximal end 102 to the distal end 104 (see, for example, FIG. 2A). In some embodiments, the fluid pathway may include an inner diameter D.

Fluid flow in a tubular fluid pathway therethrough can be analyzed using Poiseuille's equation:

$$Q = \frac{\pi D^4 \Delta P}{128 \mu L} = \frac{\Delta P}{R_f}$$

where ΔP is a change in pressure gradient across the length of the fluid pathway, D and L are the inner diameter and length, respectively, of the fluid pathway, µ is the viscosity of a fluid, and $$R_f = \frac{128 \mu L}{\pi D^4}$$

is the fluid resistance. Since µ is the viscosity of the fluid and not part of the extension tube geometry, a geometric factor $G_f$ is defined such that $R_f$ (the fluid resistance) is $$R_f = \frac{128 \mu}{\pi} G_f,$$

where $$G_f = \frac{L}{D^4}.$$

In some embodiments, the fluid pathway be tubular and may have multiple sections with lengths (L1, L2, L3) and inner diameters of (D1, D2, D3), the geometric factor is then:

$$G_f = \frac{L1}{D1^4} + \frac{L2}{D2^4} + \frac{L3}{D3^4}$$

In some embodiments, the fluid pathway may have an inner diameter that changes over the length of the fluid pathway, the geometric factor is then:

$$G_f = \int_0^L \frac{dl}{D(l)^4}$$

In some embodiments, the fluid pathway may have a cross section that is not circular or may have a complicated inner diameter profile. The geometric factor can be determined by measuring the flow rate (Q) at given pressure (ΔP) with known viscosity (µ) fluid:

$$G_f = \frac{\pi \Delta P}{128 \mu Q}$$

The $G_f$ value of the fluid pathway with the guidewire 112 in the deployed position may be selected to reduce the maximum shear stress for each catheter gauge to be the same or less than the maximum shear stress of a BD 21G VACUTAINER® UltraTouch™ push button blood collection set (available from Becton, Dickinson & Company of Franklin Lakes, New Jersey), which was previously considered the gold standard for blood draws. In some embodiments, $G_f$ value of the fluid pathway may be selected to reduce the maximum shear stress for each catheter gauge to be the same or less than the max shear stress of a BD 25G VACUTAINER® UltraTouch™ push button blood collection set (available from Becton, Dickinson & Company of Franklin Lakes, New Jersey).

In some embodiments, a LUER-LOK™ access device ("LLAD") or another suitable blood collection device may be coupled to the proximal end 102 to facilitate blood draw. In some embodiments, the LLAD may include a needle assembly, which may include a needle configured to receive a blood collection container. In these and other embodiments, the blood collection container may include an evacuated blood collection tube. In some embodiments, the blood collection container has all or a portion of air removed so pressure within the blood collection container is lower than ambient pressure. In some embodiments, the fluid pathway may include one or more of the needle assembly, the system 100 with the guidewire 112 in the deployed position, and the VAD, and may include an entirety of a blood collection pathway through which blood flows during blood collection.

The system geometric factor $G_fs$ for the fluid pathway can be determined in similar fashion as described earlier. In some embodiments, the system geometric factor $G_fs$ may be equal to or more than 7.34 E+06 (1/in³). In some embodiments, Gfs may include another value. In some embodiments, the system geometric factor $G_fs$ may be 7.34 E+06 (1/in³) plus or minus 10 percent, plus or minus 25 percent, plus or minus 50 percent, or plus or minus 75 percent. In some embodiments, Gfs may include another value, which may be selected based on a gauge and/or length of the catheter.

In some embodiments, the guidewire 112 may have a coupling feature 154 that facilitates coupling of the guidewire 112 to the retraction mechanism 114. In this context, "coupling" refers to a persistent or temporary connection by which motion of the retraction mechanism 114 can drive motion of the guidewire 112. In some embodiments, the coupling feature 154 may be located at any of various positions along the guidewire 112. In some embodiments, as illustrated in FIG. 1, the coupling feature 154 may be positioned near the proximal end 150. In some embodiments, the coupling feature 154 may have a cross-sectional shape that is generally enlarged relative to the remainder of the guidewire 112 (and more particularly, the distal end 152 of the guidewire 112 and the intermediate portion of the guidewire 112 that lies between the proximal end 150 and the distal end 152). In some embodiments, this enlarged cross-sectional shape may enable the coupling feature 154 to be coupled to the retraction mechanism 114 through the wall 139 of the tube 110.

In some embodiments, the retraction mechanism 114 may effectively pinch the tube 110 to a narrower cross section that can be moved proximally and/or distally by sliding the retraction mechanism 114 along the exterior surface 144 of the tube 110. In some embodiments, this narrower cross section may cause the interior of the tube 110 to impinge on the coupling feature 154, causing the coupling feature 154 to move proximally or distally with the retraction mechanism 114.

More specifically, in some embodiments, the retraction mechanism 114 may have a housing 160 and one or more wheels 162 carried by the housing 160. In some embodiments, the housing 160 may have an aperture 164 in which the tube 110 is received such that the tube 110 extends through the housing 160. In some embodiments, the wheels 162 may be rotatably coupled to the housing 160, and may be positioned to press against the exterior surface 144 of the tube 110 within the housing 160. In some embodiments, the retraction mechanism 114 may have two wheels 162 positioned on opposite sides of the housing 160. In alternative embodiments, a retraction mechanism may have more or fewer than two wheels. In some embodiments, many other alternative structures exist, as will be described in connection with subsequent embodiments.

Figure 2A:
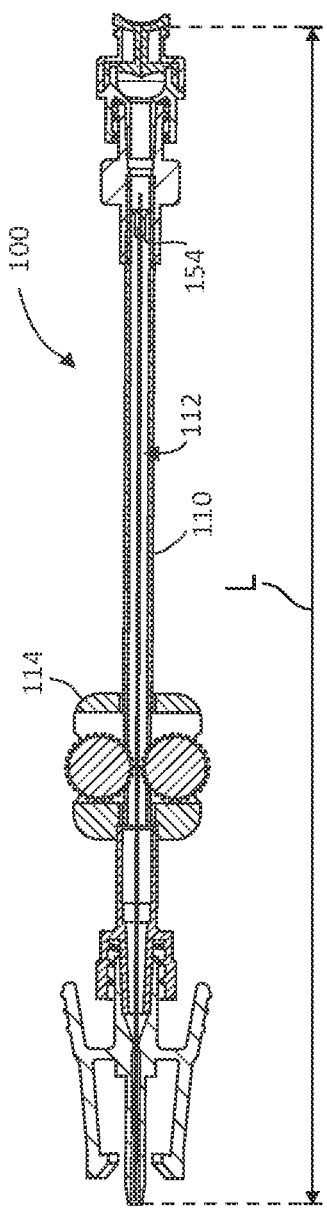
FIGS. 2A, 2B, and 2C are front elevation, section views of the system of FIG. 1, in a pre-deployment position, a deployed position, and a retracted position, respectively, according to some embodiments.

Referring now to FIG. 2, FIGS. 2A, 2B, and 2C are front elevation, section views of the system of FIG. 1, in a pre-deployment position, a deployed position, and a retracted position, respectively. In some embodiments, a user may commence with the system 100 in a pre-deployment position, as illustrated in FIG. 2A. From the pre-deployment position, the user may deploy the guidewire 112 into the patient's vascular system, moving the system 100 to the deployed position of FIG. 2B. In some embodiments, in response to the patient's treatment being completed, the system 100 may be moved to the retracted position of FIG. 2C, by sliding the retraction mechanism 114 proximally.

In some embodiments, in operation, with the system 100 in the pre-deployment position of FIG. 2A, the user may couple the system 100 to an existing VAD, for example, by inserting the distal connector 136 into a female receiver of the VAD and securing the clip 138 to the VAD. In some embodiments, the user may further couple the system 100 to a source of pressurized fluid, such as a syringe, by coupling the proximal connector 126 to the source. In some embodiments, pressurized fluid at the proximal end 102 of the system 100 may press against the proximal surface(s) of the coupling feature 154 of the guidewire 112, thereby driving the guidewire 112 distally from the retracted position to the deployed position of FIG. 2B. This process may be called "flushing." In some embodiments, the saline solution may be injected into the vascular system, or in some embodiments, may be vented out of the system 100 near the proximal end 102 of the system 100 through a valve (not illustrated) or the like.

In some embodiments, in the pre-deployment position of FIG. 2A, the retraction mechanism 114 may be positioned proximate the distal end 142 of the tube 110 so that the retraction mechanism 114 does not interfere with deployment of the guidewire 112. In some embodiments, the position of the retraction mechanism 114 may control the extent to which the guidewire 112 is able to deploy. In some embodiments, a user may make use of this property by sliding the retraction mechanism 114 to a desired position, along the tube 110, prior to deployment of the guidewire 112. For example, a longer VAD may necessitate deployment of the guidewire 112 with greater motion to enable the distal end 152 of the guidewire 112 to reach the patient's vascular system. Conversely, a shorter VAD may enable deployment with less motion. Further, the user may wish to control how far the distal end 152 of the guidewire 112 extends into the vascular system of the patient.

Thus, in some embodiments, the user may optionally slide the retraction mechanism 114, prior to deployment, to a position between the proximal end 140 and the distal end 142 of the tube 110 to cause such shorter deployment to occur. In some embodiments, the retraction mechanism 114 may pinch the tube 110 within the housing 160 so that the coupling feature 154 of the guidewire 112 is unable to move through the housing 160.

Figure 2B:
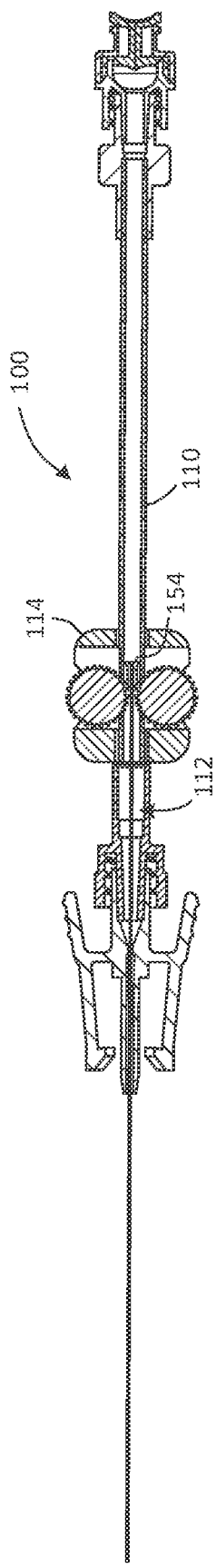
Figure 2C:
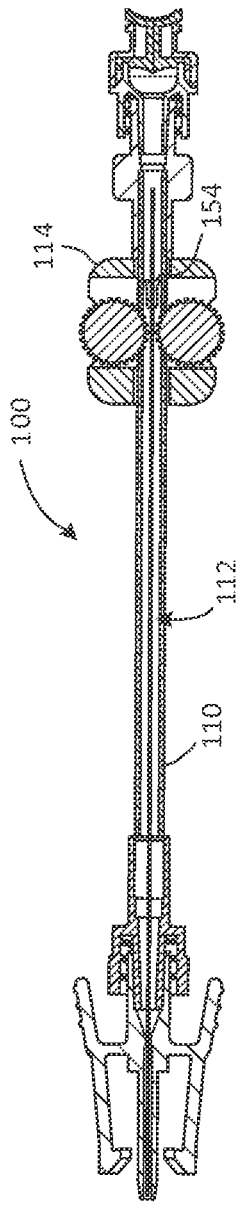

In some embodiments, in the deployed position of FIG. 2B, the user may carry out one or more actions relative to the patient's vascular system, using the access provided by the system 100 with the guidewire 112 deployed into the vascular system. In some embodiments, once the one or more actions are complete, the user may wish to remove the system 100 from the VAD, necessitating motion of the system 100 back to the retracted position. Thus, the user may slide the retraction mechanism 114 back toward the proximal end 140 of the tube 110. In some embodiments, the pinched section of the tube 110 within the housing 160 of the retraction mechanism 114 may also move proximally, pushing the coupling feature 154 proximally as well. In some embodiments, the guidewire 112 may thus move proximally until the guidewire 112 is again contained within the tube 110 and the system 100 is in the retracted position of FIG. 2C. In some embodiments, the user may then disconnect the distal connector 136 from the VAD without exposing themselves to blood. In some embodiments, optionally, a valve (not illustrated) may be present proximate the distal end 104 of the system 100; the valve may be closed after retraction of the guidewire 112.

Figure 3:
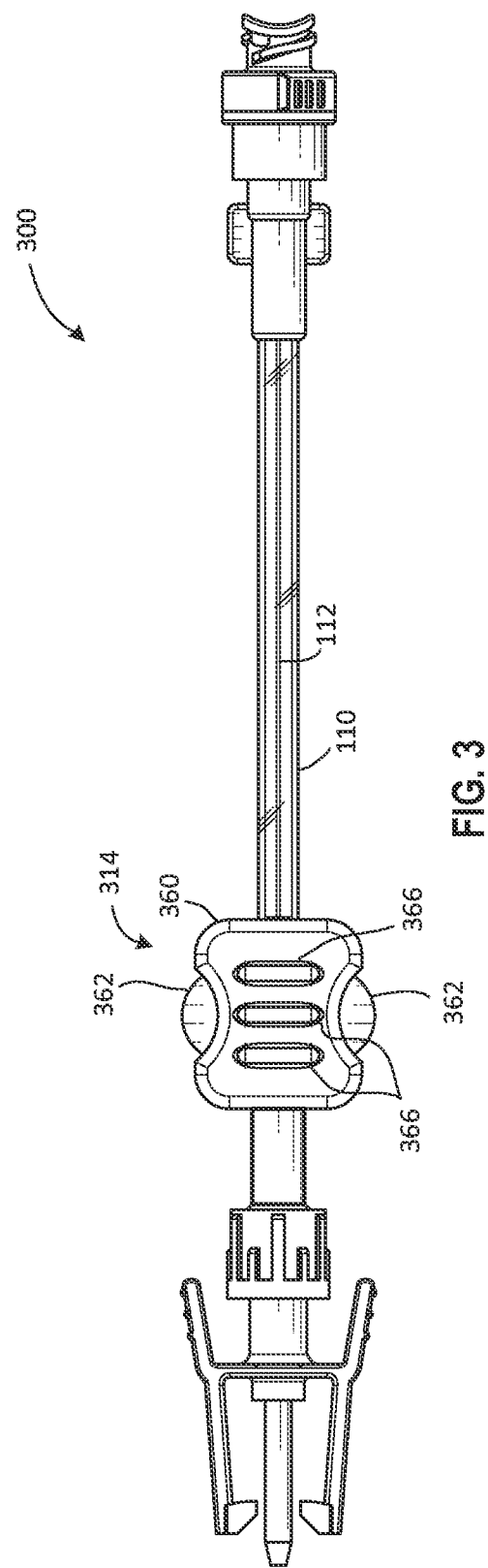
FIG. 3 is a front elevation view of a system for accessing a patient's vascular system, according to some embodiments.

Referring now to FIG. 3, FIG. 3 is a front elevation view of a system 300 for accessing a patient's vascular system, according to some embodiments. In some embodiments, the system 300 may have a configuration similar to that of the system 100 of FIG. 1, except that the system 300 has a retraction mechanism 314 with a modified design. Specifically, in some embodiments, the retraction mechanism 314 may have a housing 360 with grip features 366 that enhance a user's ability to grasp and slide the housing 360 along the tube 110. In some embodiments, the grip features 366 may be ridges, indentations, surface texturing such as knurling, and/or any other features that make the housing 360 easier to grip and move. In some embodiments, the retraction mechanism 314 may further have wheels 362 with smooth, rather than ridged, edges.

Figure 4A:
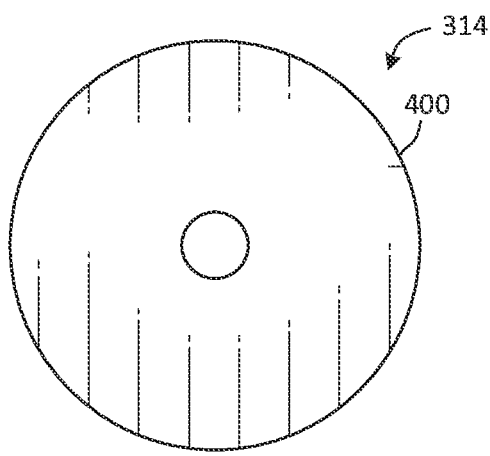
FIGS. 4A and 4B are front elevation views of smooth and ridged wheels, respectively, that may be used in connection the systems of FIGS. 3 and 1, respectively, according to some embodiments.
Figure 4B:
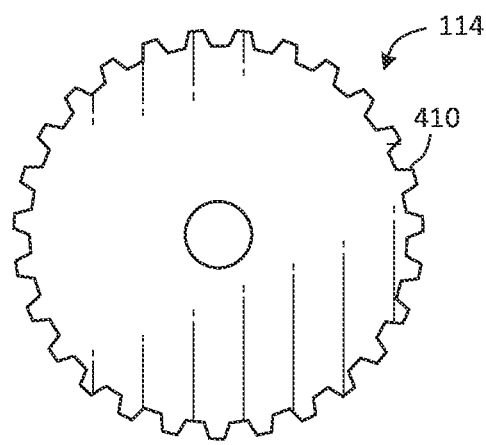

Referring now to FIG. 4, FIGS. 4A and 4B are front elevation views of smooth wheels and ridged wheels, respectively, that may be used in connection the systems of FIGS. 3 and 1, respectively, according to some embodiments. In some embodiments, the smooth edges 400 of the wheels 362 may make the retraction mechanism 314 easier to slide in the embodiment of FIG. 3. In some embodiments, the ridged edges 410 of the wheels 162 of the retraction mechanism 114 may be easier for a user to grasp and rotate in order to urge the retraction mechanism 114 to slide along the tube 110 in the embodiment of FIG. 1.

In other embodiments, wheels such as the wheels 162 or the wheels 362 may be fully enclosed within a housing such that they cannot be seen or touched by the user. Such a configuration may advantageously streamline the appearance of the device and eliminate potential pinch points.

Referring now to FIG. 5, FIGS. 5A, 5B, and 5C are front elevation views of a system 500 for accessing a patient's vascular system according to some embodiments, in a pre-compression state, a mid-compression state, and a post-compression state, respectively. In some embodiments, the system 500 may be configured in a manner similar to that of the system 100 of FIG. 1, except that deployment and/or retraction may be carried out via manual compression of the tube 110.

More specifically, in some embodiments, the system 500 may have a tube 110 like that of FIG. 1, a guidewire 512, and a retraction mechanism 514. In some embodiments, the guidewire 512 may have a proximal end 550, a distal end 552, and a coupling feature 554 positioned near the proximal end 550. In some embodiments, the coupling feature 554 may protrude outward toward the interior of the tube 110 so that the tube 110 can be compressed to grip the coupling feature 554 through the tube 110. In some embodiments, the retraction mechanism 514 may be configured as a compression ring that can be compressed, elastically, by hand, or via application of other compressive force (for example via a tool such as a crimper or the like) to grip the exterior surface 144 of the wall 139 of the tube 110.

Figure 5A:
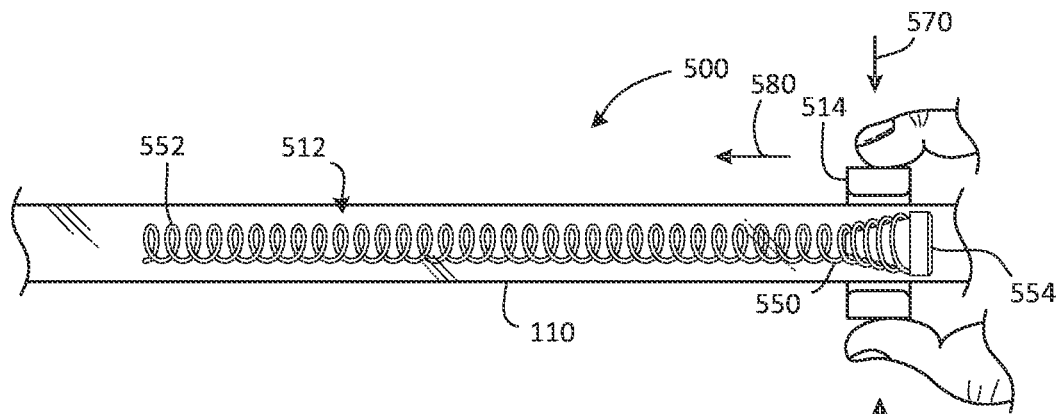
FIGS. 5A, 5B, and 5C are front elevation views of a system for accessing a patient's vascular system, in a pre-compression state, a mid-compression state, and a post-compression state, respectively, according to some embodiments.
Figure 5B:
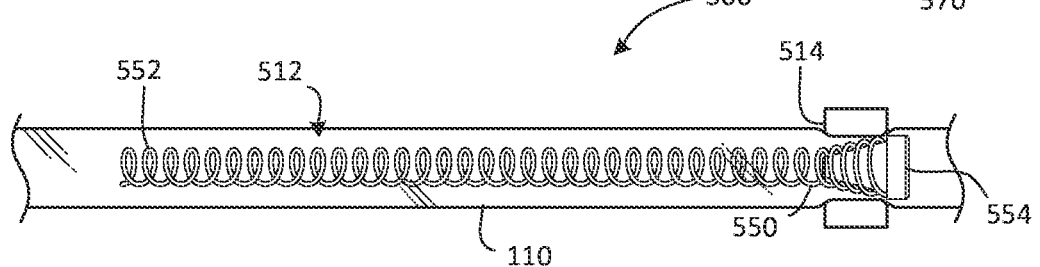
Figure 5C:
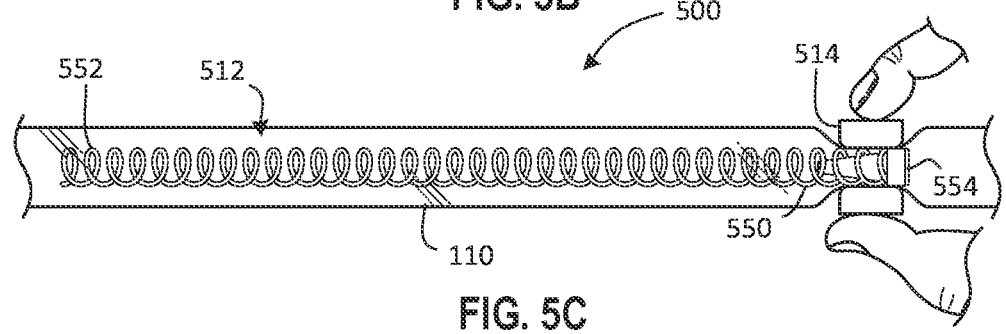

As illustrated in FIG. 5A, in some embodiments, the coupling feature 554 may be compressible by hand along the directions illustrated by the arrows 570 so that the coupling feature grips the exterior surface 144 of the wall 139 of the tube 110. FIG. 5B illustrates the system 500 with some compression applied, according to some embodiments. FIG. 5C illustrates the system 500 with full compression applied, according to some embodiments. In some embodiments, the retraction mechanism 514 can be moved along the tube 110 to urge the coupling feature 554 to move proximally or distally, as illustrated by the arrow 580.

Thus, in some embodiments, the retraction mechanism 514 may be used as a deployment mechanism in addition to, or in the alternative to, a retraction mechanism. In some embodiments, rather than deploying the guidewire 512 via flushing the tube 110 with pressurized fluid, the guidewire 512 may be manually deployed with the retraction mechanism 514. In some embodiments, the guidewire 512 may then be manually retracted, also through the use of the retraction mechanism 514 by squeezing the retraction mechanism 514 as illustrated by the arrows 570, and then sliding the retraction mechanism 514 proximally. In some embodiments, the guidewire 512 may instead be deployed via flushing, and then retracted with the retraction mechanism 514.

Figure 6:
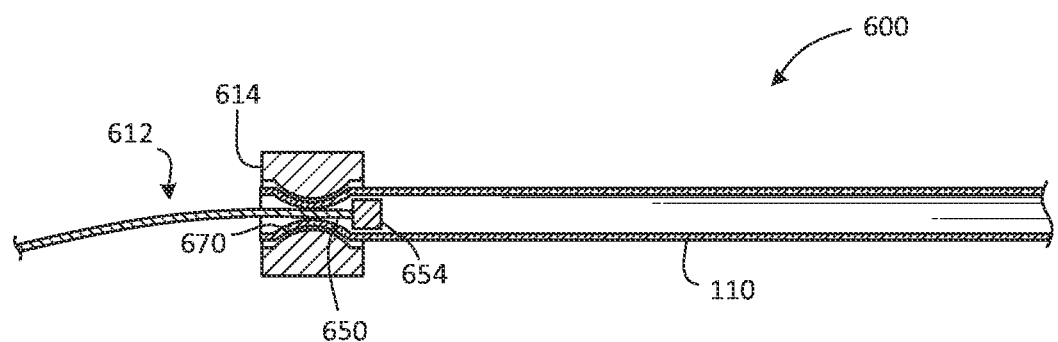
FIG. 6 is a front elevation view of a system for accessing a patient's vascular system, according to some embodiments.
Figure 7A:
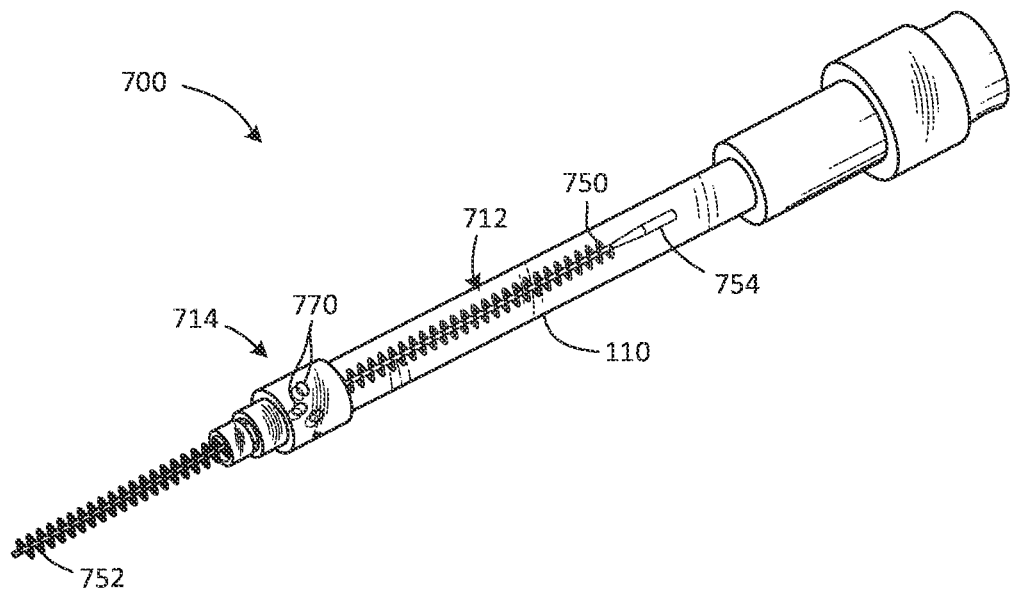
FIGS. 7A, 7B, and 7C are perspective, front elevation, section, and side elevation, section views, respectively, of a system for accessing a patient's vascular system, according to some embodiments.
Figure 7B:
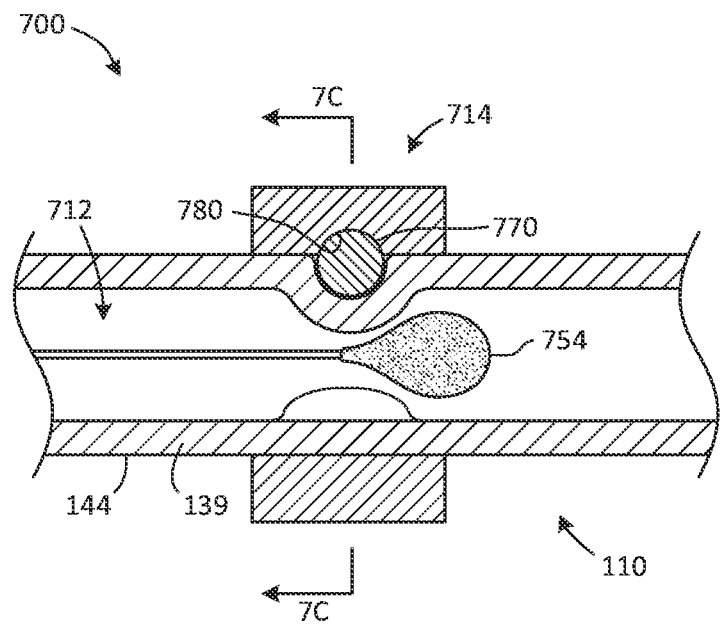
Figure 7C:
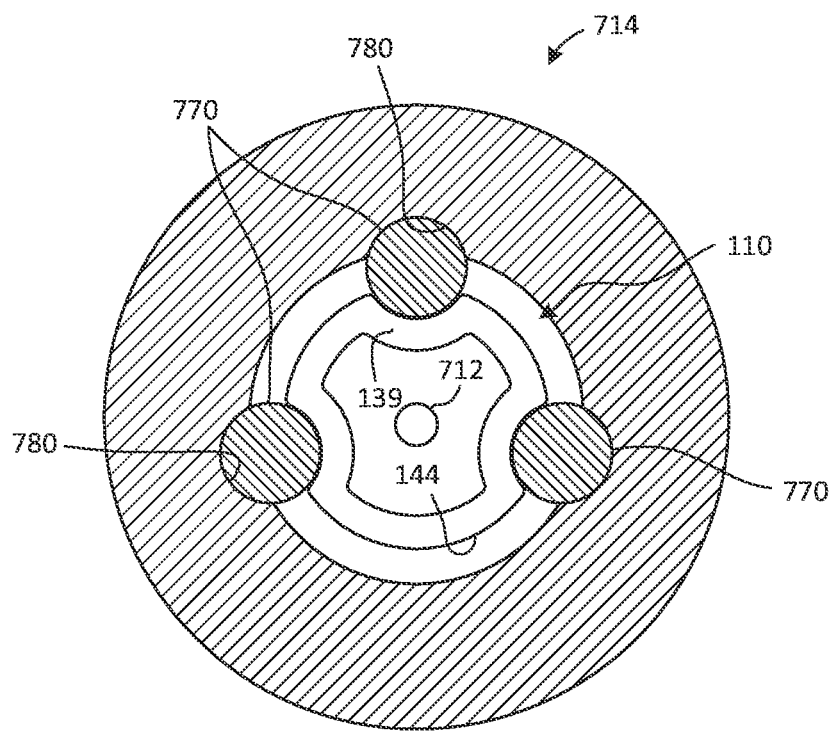

Referring now to FIG. 6, FIG. 6 is a front elevation view of a system 600 for accessing a patient's vascular system, according to some embodiments. In some embodiments, the system 600 may be configured in a manner similar to that of the system 100 of FIG. 1, except that deployment and/or retraction may be carried out without the use of wheels such as the wheels 162 or the wheels 362.

More specifically, in some embodiments, the system 600 may have a tube 110 like that of FIG. 1, a guidewire 612, and a retraction mechanism 614. In some embodiments, the guidewire 612 may have a proximal end 650, a distal end (not illustrated), and a coupling feature 654 positioned near the proximal end 650. In some embodiments, the coupling feature 654 may protrude outward, but need not be directly engaged by the interior of the tube 110. Rather, in some embodiments, the retraction mechanism 614 may be configured as a ring with a convex inward protrusion 670 that presses inward continuously against the exterior surface 144 of the wall 139 of the tube 110. In some embodiments, the pinched interior diameter of the tube 110 may be too small to permit passage of the coupling feature 654 therethrough. Thus, in some embodiments, the retraction mechanism 614 may be used to push the coupling feature 654 either proximally or distally in order to deploy or retract the guidewire 612.

Referring now to FIG. 7, FIGS. 7A, 7B, and 7C are perspective, front elevation, section, and side elevation, section views, respectively, of a system for accessing a patient's vascular system according to another alternative embodiment. In some embodiments, the system 700 may be configured in a manner similar to that of the system 100 of FIG. 1, except that deployment and/or retraction may be facilitated through the use of ball bearings.

More specifically, in some embodiments, the system 700 may have a tube 110 like that of FIG. 1, a guidewire 712, and a retraction mechanism 714. The guidewire 712 may have a proximal end 750, a distal end 752, and a coupling feature 754 positioned near the proximal end 750. In some embodiments, the retraction mechanism 714 may have one or more ball bearings 770 that press against the exterior surface 144 of the wall 139 of the tube 110, causing the interior surface of the tube 110 within the retraction mechanism 714 to be too small to permit passage of the coupling feature 754 therethrough.

In some embodiments, the ball bearings 770 may be rotatable within sockets 780 formed in the interior of the retraction mechanism 714, facing toward the exterior surface 144 of the wall 139 of the tube 110. In some embodiments, rotation of the ball bearings 770 may make it easier to slide the retraction mechanism 714 along the tube 110. In some embodiments, the retraction mechanism 714 may otherwise function in a manner similar to that of the system 600 of FIG. 6, and may be used to deploy or retract the guidewire 712. In some embodiments, the system 600 has three ball bearings distributed radially symmetrically about the axis of the retraction mechanism; however, in other embodiments, one, two, or more than three ball bearings may be present, and may be arranged in a variety of symmetrical and asymmetrical arrangements.

Figure 8A:
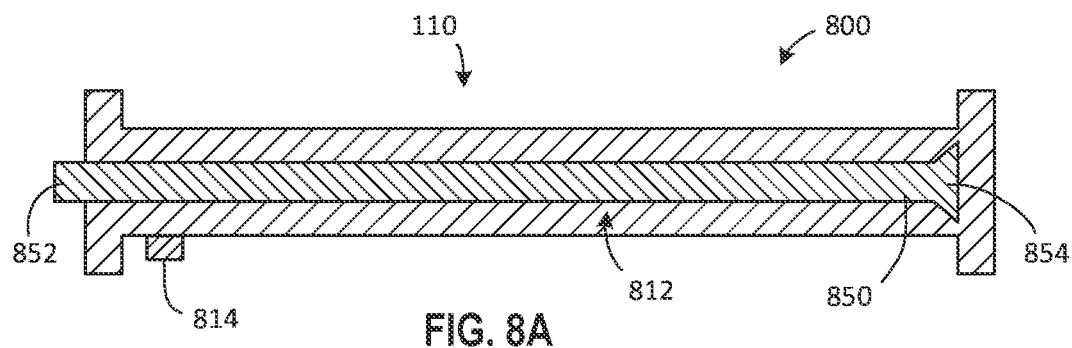
FIGS. 8A and 8B are front elevation, schematic section views of systems for accessing a patient's vascular system, according to some embodiments.
Figure 8B:
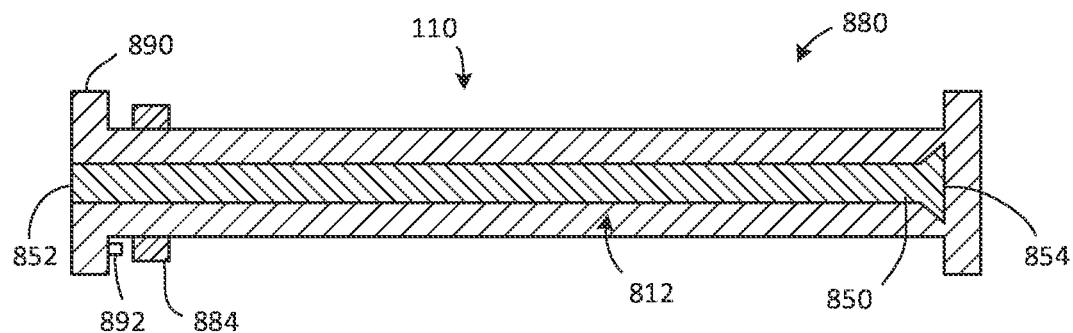

Referring now to FIG. 8, FIGS. 8A and 8B are front elevation, schematic section views of a system 800 and a system 880, respectively, for accessing a patient's vascular system, according to some embodiments. In some embodiments, the system 800 and the system 880 may each be configured in a manner similar to that of the system 100 of FIG. 1, except that deployment and/or retraction may be carried out through the use of magnetism.

More specifically, in some embodiments, the system 800 may have a tube 110 like that of FIG. 1, a guidewire 812, and a retraction mechanism 814. In some embodiments, the guidewire 812 may have a proximal end 850, a distal end 852, and a coupling feature 854 positioned near the proximal end 650. In some embodiments, the coupling feature 854 may be magnetic, or may be made of a magnetic material such as a ferromagnetic material. In some embodiments, the retraction mechanism 814 may also be magnetic, or may be made of a magnetic material such as a ferromagnetic material, selected such that there is either attraction or repulsion between the coupling feature 854 and the retraction mechanism 814. In some embodiments, the retraction mechanism 814 may encircle the tube 110, or may be simply slidably coupled to one side of the tube 110 as illustrated.

Referring now to FIG. 8, FIG. 8A depicts the system 800 in the pre-deployment position. In some embodiments, as the guidewire 812 deploys, it may move distally (i.e., leftward in FIG. 8A), bringing the coupling feature 854 close to the retraction mechanism 814. Then, in order to retract the guidewire 812, the coupling feature 854 may be moved proximally (i.e., rightward in FIG. 8A). In some embodiments, repulsion between the retraction mechanism 814 and the coupling feature 854 may cause the retraction mechanism 814 to push the coupling feature 854 proximally, ahead of it. In some embodiments, attraction between the retraction mechanism 814 and the coupling feature 854 may cause the retraction mechanism 814 to draw the coupling feature 854 proximally, behind it. In some embodiments, in either case, proximal motion of the retraction mechanism 814 may cause proximal motion of the guidewire 812 to the retracted position, by virtue of magnetic coupling between the coupling feature 854 and the retraction mechanism 814.

Notably, in some embodiments, the retraction mechanism 814 and the coupling feature 854 may both be magnetized, with relative polarity that provides the desired attraction or repulsion. However, in some embodiments, only one of the retraction mechanism 814 and the coupling feature 854 are magnetized; the other may simply provide a low reluctance pathway for the magnetic field generated by the other, leading to attraction between the two. In some embodiments, if desired, the retraction mechanism 814 may be used to deploy the guidewire 812, in addition to or in the alternative to retracting the guidewire 812.

In some embodiments, the system 880 of FIG. 8B is similar. However, in some embodiments, a retraction mechanism 884 of the system 880 may have a ring-shape that encircles, or substantially encircles, the tube 110. In some embodiments, the tube 110 may be coupled, at the distal end 142 of the tube 110, to a magnetic hub 890 that attracts the retraction mechanism 884 to hold it in place until retraction of the guidewire 812 is to be carried out. Thus, in some embodiments, one or both of the magnetic hub 890 and the retraction mechanism 884 may be magnetic. In some embodiments, one may be formed of a magnetic material, such as a ferromagnetic material. In some embodiments, the system 880 may further have a spacer 892 that resides between the retraction mechanism 884 and the magnetic hub 890 to facilitate separation of the retraction mechanism 884 from the magnetic hub 890 when the time comes to retract the guidewire 812.

Figure 9:
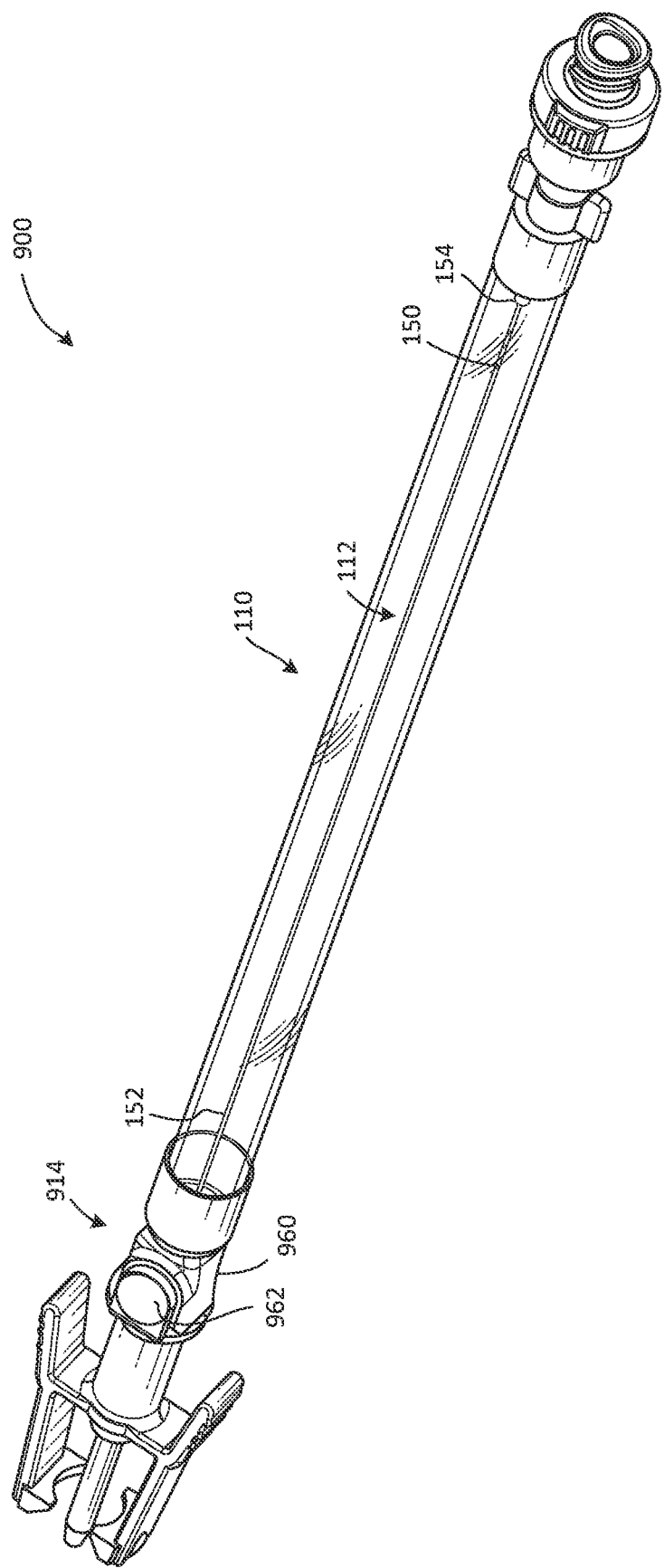
FIG. 9 is a perspective view of a system for accessing a patient's vascular system, according to some embodiments.

Referring now to FIG. 9, FIG. 9 is a perspective view of a system 900 for accessing a patient's vascular system, according to some embodiments. In some embodiments, the system 900 may be configured in a manner similar to that of the system 100 of FIG. 1, except that retraction may be driven by a spring.

More specifically, in some embodiments, the system 900 may have a tube 110 and a guidewire 112 like those of FIG. 1, and a retraction mechanism 914. In some embodiments, the retraction mechanism 914 may include a housing 960 with a button 962 coupled to a spring 964 that is retained in a compressed state until retraction is to be carried out.

Referring now to FIG. 10, FIGS. 10A and 10B are front elevation views of the system of FIG. 9, prior to deployment and after retraction, respectively, according to some embodiments. In some embodiments, prior to deployment, as illustrated in FIG. 10A, the spring 964 resides within the housing 960. In some embodiments, when retraction is desired, the user may press the button 962 to release a catch (not illustrated) within the housing 960 to release the spring 964, allowing the spring 964 to extend distally and push the coupling feature 154 in the distal direction. In some embodiments, the spring 964 may have an interior diameter sufficient to slide over the distal end 152 of the guidewire 112, but small enough that the spring 964 is unable to pass beyond the coupling feature 154. Thus, in some embodiments, expansion of the spring 964 urges the coupling feature 154, and thence the guidewire 112, to move distally to the retracted position illustrated in FIG. 10B.

Referring now to FIG. 11, FIGS. 11A, 11B, and 11C are front elevation, section views of a system 1100 for accessing a patient's vascular system, according to some embodiments, prior to deployment, after deployment, prior to retraction, and after retraction, respectively. In some embodiments, the system 1100 may be similar to the system 900 of FIG. 9, but with springs used to drive both deployment and retraction.

More specifically, in some embodiments, the system 1100 may have a tube 110 and a guidewire 112 like those of FIG. 1, a retraction mechanism 1114, and a deployment mechanism 1116. In some embodiments, each of the retraction mechanism 1114 and the deployment mechanism 1116 may include a spring that is, in the pre-deployment state of FIG. 11A, retained in a compressed state. In some embodiments, the retraction mechanism 1114 may include a spring 1160, and the deployment mechanism 1116 may include a spring 1170. In some embodiments, the spring 1160 of the retraction mechanism 1114 may reside within a tubular housing 1180, and the spring 1170 of the deployment mechanism 1116 may reside outside of and generally encircle the tubular housing 1180.

In some embodiments, the retraction mechanism 1114 and the deployment mechanism 1116 may each further include a catch (not illustrated) that holds the associated spring in the compressed state until the time of retraction or deployment, respectively, and a button, lever, or other user control (not illustrated) that enables the catch to be released to initiate retraction or deployment, respectively. Thus, the user may actuate the appropriate control to initiate deployment or retraction.

Figure 11A:
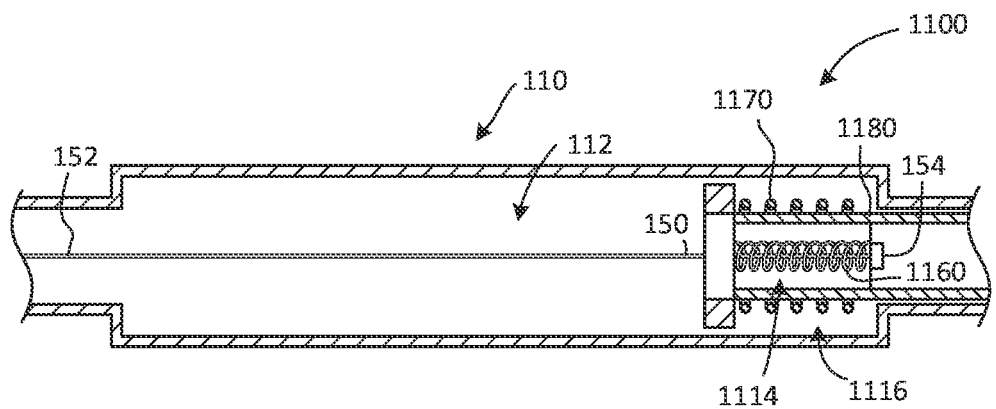
FIGS. 11A, 11B, and 11C are front elevation, section views of a system for accessing a patient's vascular system, prior to deployment, after deployment, prior to retraction, and after retraction, respectively, according to some embodiments.
Figure 11B:
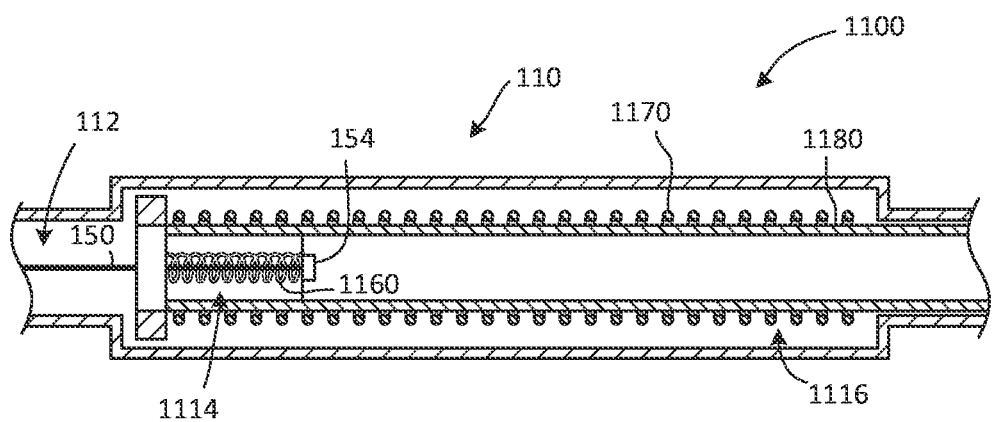
Figure 11C:
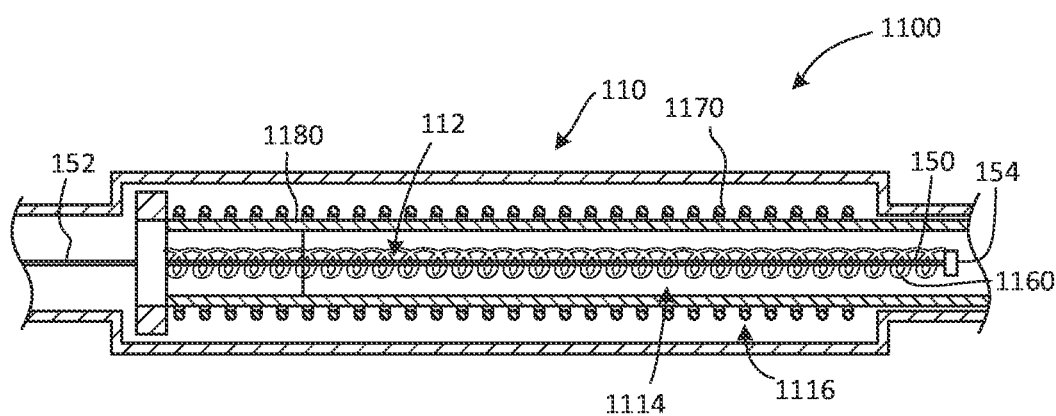

In some embodiments, initially, the spring 1160 and the spring 1170 may both be in the compressed state, as illustrated in FIG. 11A. In some embodiments, when the user initiates deployment, the spring 1170 may be allowed to expand, pushing the tubular housing 1180 and the guidewire 112 distally. In some embodiments, the tubular housing 1180 may come to rest proximate the distal end 142 of the tube 110, as in the deployed configuration of FIG. 11B.

In some embodiments, when the user initiates retraction, the spring 1160 may be allowed to expand, pushing the guidewire 112 proximally. In some embodiments, the tubular housing 1180 may remain in place. Thus, in some embodiments, the system 1100 may reach the retracted configuration of FIG. 11C, in which the spring 1160 and the spring 1170 are both extended and relatively relaxed.

Referring now to FIG. 12, FIGS. 12A, 12B, and 12C are front elevation, schematic, deployed, front elevation deployed, and front elevation, retracted views, respectively, of a system 1200 for accessing a patient's vascular system, according to some embodiments. In some embodiments, the system 1200 may be similar to the system 100 of FIG. 1, with a tether used to carry out retraction.

Figure 12A:
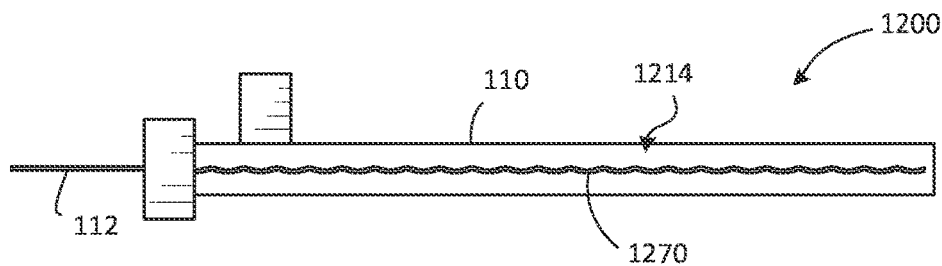
FIGS. 12A, 12B, and 12C are front elevation, schematic, deployed, front elevation deployed, and front elevation, retracted views, respectively, of a system for accessing a patient's vascular system, according to some embodiments.

More specifically, in some embodiments, as illustrated in FIG. 12A, the system 1200 may have a tube 110 and a guidewire 112 like those of FIG. 1, and a retraction mechanism 1214 including a tether 1270. In some embodiments, the tether may be secured to the coupling feature 154 of the guidewire 112, and may extend proximally from the coupling feature 154 and exit the system 1200 so that the user can pull a free end of the tether 1270 to retract the guidewire 112 from the deployed position to the retracted position.

Figure 12B:
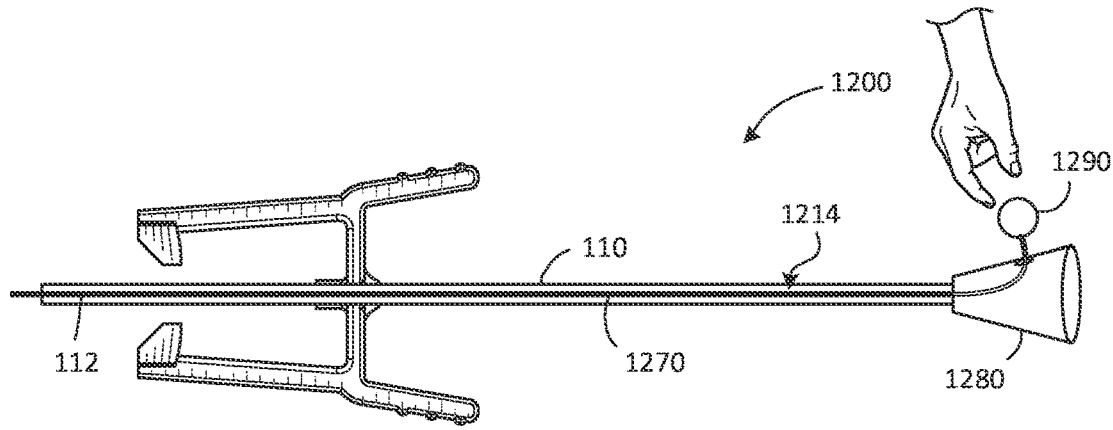

As illustrated in FIG. 12B, in some embodiments, the system 1200 may include a housing 1280, positioned proximal to the tube 110, through which the free end of the tether 1270 exits and is accessible to the user. In some embodiments, the free end may have a grip 1290 such as a ball or knob that can be easily grasped by hand and pulled. In the deployed position of FIG. 12B, the grip 1290 may reside near the housing 1280, with little or none of the tether 1270 exposed between the housing 1280 and the grip 1290. In some embodiments, pulling the grip 1290 may draw the guidewire 112 to the retracted position as the grip 1290 moves away from the housing 1280, exposing more of the tether 1270 outside the housing 1280.

Figure 12C:
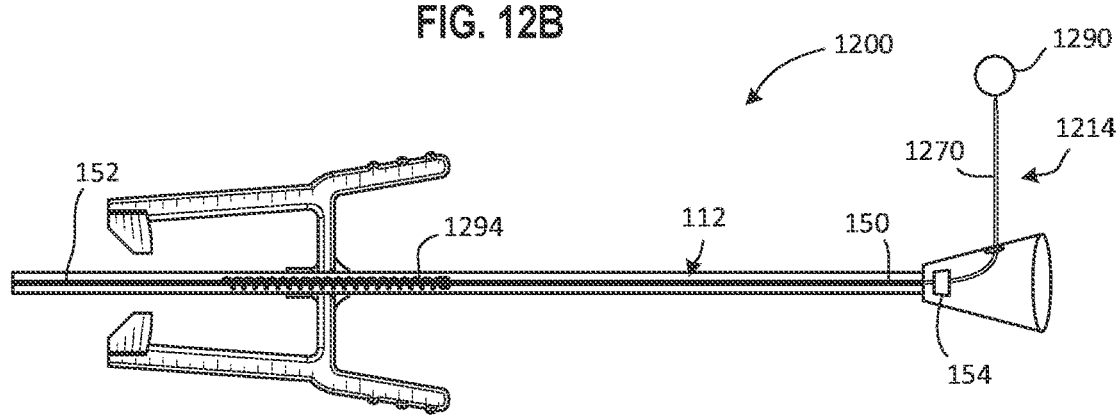

As illustrated in FIG. 12C, in some embodiments, a spring 1294 may be coupled to the guidewire 112 to keep the guidewire 112 in the deployed position until the tether 1270 is drawn proximally by the user. Thus, the user may optionally pull against the force of the spring 1294 to retract the guidewire 112.

Figure 13:
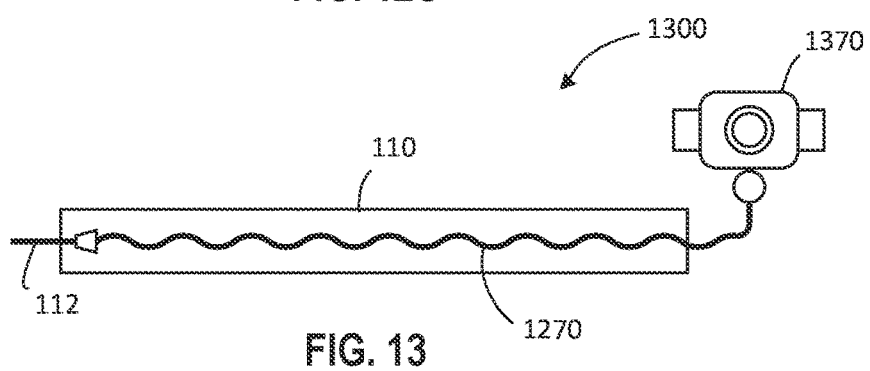
FIG. 13 is a front elevation, schematic view of a system for accessing a patient's vascular system, according to some embodiments.

Referring now to FIG. 13, FIG. 13 is a front elevation, schematic view of a system 1300 for accessing a patient's vascular system, according to some embodiments. In some embodiments, the system 1300 may be similar to the system 1200 of FIGS. 12A, 12B, and 12C, with a tether used to carry out retraction. However, in some embodiments, the system 1300 may also include a rotary windup 1370 that receives and winds the tether during retraction. The rotary windup 1370 may be hand-operated (for example, via a crank or the like), or may be driven by a spring, motor, or other device.

Figure 14A:
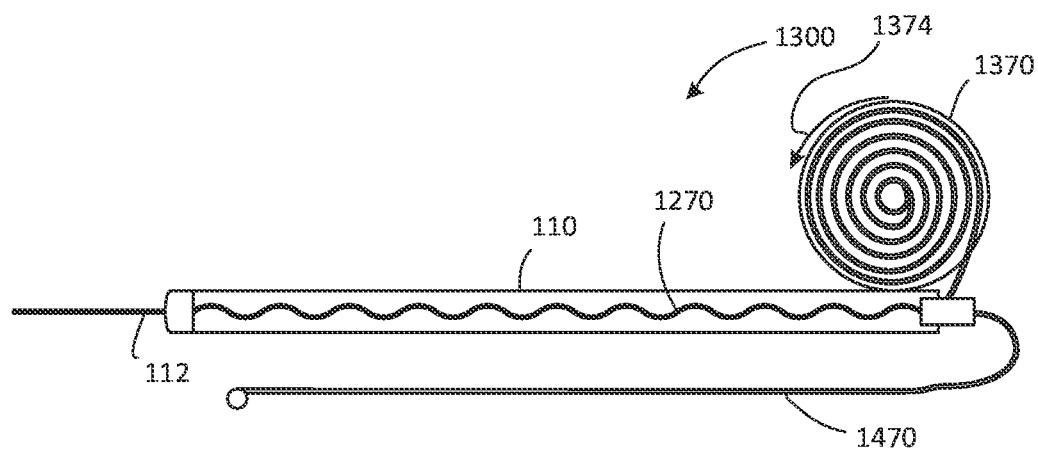
FIGS. 14A and 14B are front elevation, schematic and perspective views of the system of FIG. 13, according to some embodiments.
Figure 14B:
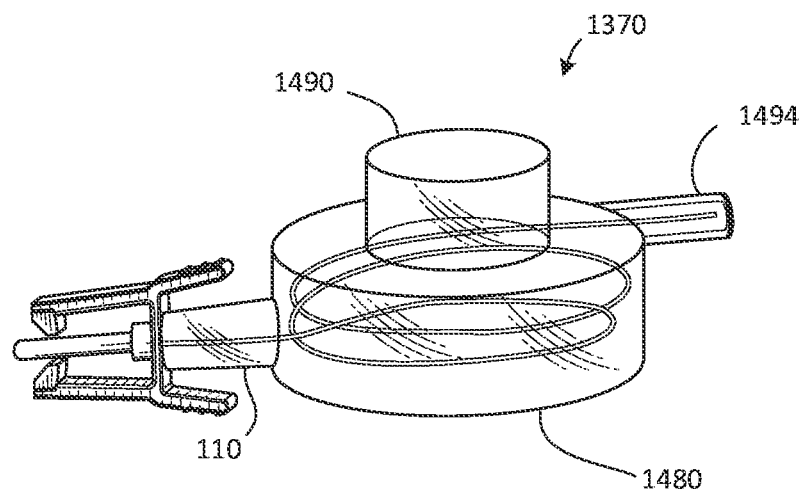

Referring now to FIG. 14, FIGS. 14A and 14B are front elevation, schematic and perspective views of the system 1300 of FIG. 13, according to some embodiments. FIG. 14A illustrates the optional use of electrical power, delivered via a wire 1470, to power a motor (not illustrated) in the rotary windup 1370, according to some embodiments. In some embodiments, the rotary windup 1370 may have a spindle (not illustrated) about which the proximal end of the tether 1270 is wound; the spindle may rotate in the direction indicated by the arrow 1374 in order to take up the tether 1270 and draw the guidewire 112 to the retracted position.

FIG. 14B illustrates the rotary windup 1370 in greater detail, according to some embodiments. In some embodiments, the rotary windup 1370 may include a housing 1480 to receive the tether 1270, a motor compartment 1490 that stores an electric motor, spring, or other driver, and an aspiration port 1494 connectable to a fluid receptacle. In some embodiments, blood and/or other liquids may be aspirated from the tube 110, through the rotary windup 1370, and out of the system 1300 through the aspiration port 1494. Other rotary windup mechanisms that may be used in connection with such embodiments are illustrated and described in U.S. patent application Ser. No. 16/388,650, filed Apr. 18, 2019, entitled INSTRUMENT DEVLIERY DEVICE HAVING A ROTARY ELEMENT, which is incorporated herein by reference.

Referring now to FIG. 15, FIGS. 15A, 15B are front elevation, schematic views of a system 1500 for accessing a patient's vascular system, according to some embodiments, in the deployed and retracted positions, respectively. In some embodiments, in addition to or in the alternative to retraction of a guidewire into a tube, a system may have a protective shield that extends to cover the guidewire in the deployed configuration. In some embodiments, such a protective shield may contain blood and/or other fluids from the surgical site, thereby helping practitioners avoid contact with potential pathogens.

More specifically, in some embodiments, the system 1500 may have a tube 110 and a guidewire 112 like those of the system 100 of FIG. 1. However, in some embodiments, the system 1500 may not include a retraction mechanism, but instead may have a protective shield 1514 that can be extended distally, from the distal end 142 of the tube 110, to cover the guidewire 112 after deployment of the guidewire 112. In some embodiments, the protective shield 1514 may include an extensible member 1560 and a collar 1562 at the distal end of the extensible member 1560. In some embodiments, the extensible member 1560 have an accordion configuration or the like, that allows the extensible member 1560 to be effectively stretched along its axis. In some embodiments, the collar 1562 may facilitate provision of a fluid seal while the guidewire 112 is deployed within the patient's vascular system and/or while the system 1500 is being removed from the VAD.

FIG. 15A illustrates the system 1500 in the deployed position, with the extensible member 1560 in the compacted configuration to allow the guidewire 112 to protrude beyond the collar 1562, according to some embodiments. In some embodiments, the exposed portion of the guidewire 112 may reside within the VAD and/or the patient's vascular system (not illustrated) during performance of one or more actions requiring access to the vascular system. In some embodiments, after the actions are complete, rather than retracting the guidewire 112 back into the tube 110, the guidewire 112 may remain deployed relative to the tube 110, but may be covered by extending the extensible member 1560 such that the guidewire 112 is contained within the protective shield 1514, as illustrated in FIG. 15B. FIGS. 15A and 15B are schematic views that omit details of the system 1500, some of which will be illustrated in FIGS. 15C and 15D, according to some embodiments.

FIGS. 15C and 15D are front elevation views of the distal end of a system 1580 for accessing a patient's vascular system according to some embodiments, in the retracted configuration, with a protective shield 1590 attached to and detached from a VAD, respectively. In some embodiments, the system 1580 may be configured substantially the same as the system 1500 of FIGS. 15A and 15B, except that the system 1580 has a protective shield 1590 with a collar 1592 that has a coupling feature 1594 that can be used to removably couple the distal end of the protective shield 1590 to another device, such as the VAD 1596, to form a fluid seal. In some embodiments, the coupling feature 1594 may, in some examples, take the form of a pair of arms that extend proximally and bend inward to slide into corresponding slots 1599 in the VAD 1596. In some embodiments, various detents, locking features, and/or other devices (not illustrated) may be used to ensure that the arms remain engaged within the slots 1599 until deliberately removed by the user.

In some embodiments, in the sealed configuration of FIG. 15C, blood and/or other fluids may be retained within the protective shield. In some embodiments, when the system 1500 is to be decoupled from the VAD 1596, the system 1500 may be oriented with the protective shield 1590 upward to ensure that any fluid trapped within the protective shield 1590 does not leak out of the protective shield 1590. Then, in some embodiments, the arms may be decoupled from the VAD 1596 as illustrated in FIG. 15D. Then, in some embodiments, if desired, a cap or other sealable feature (not illustrated) may be coupled to the coupling feature 1594 to seal the protective shield 1590, containing the otherwise exposed portion of the guidewire 112 and associated fluids, to avoid fluid leakage during subsequent storage, transportation, and/or disposal.

Figure 16A:
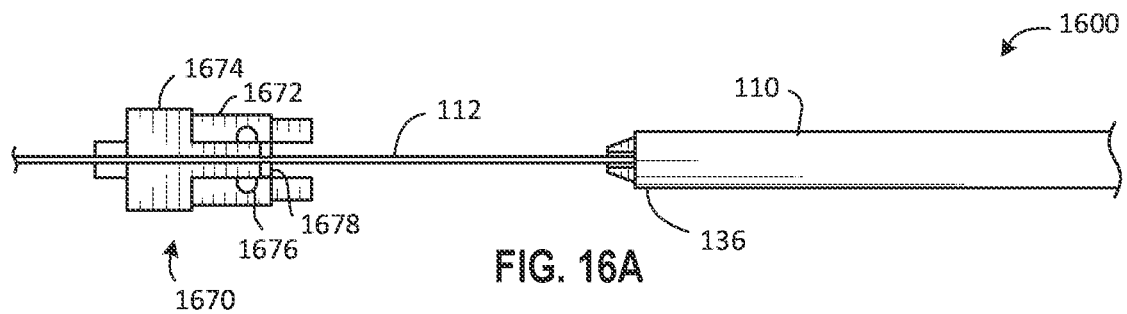
FIGS. 16A and 16B are front elevation, partial section views of a system for accessing a patient's vascular system, according to some embodiments.
Figure 16B:
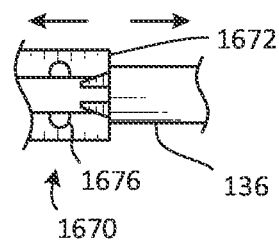

Referring now to FIG. 16, FIGS. 16A and 16B are front elevation, partial section views of a system 1600 for accessing a patient's vascular system, according to some embodiments. In some embodiments, in the alternative to retracting the guidewire 112 and covering the guidewire 112 with a protective shield, a cleaning module may be used to clean blood and/or other fluids form the guidewire 112. In some embodiments, the cleaning module may slide along the guidewire 112 to absorb fluids and remove fluids with a squeegee effect.

FIG. 16A illustrates the distal end of the system 1600 and a cleaning module 1670 that may be used to clean the guidewire 112 rather than retracting or covering the guidewire 112, according to some embodiments. In some embodiments, the cleaning module 1670 may be designed to both absorb and remove fluids. Specifically, in some embodiments, the cleaning module 1670 may have a housing 1672 and a cap 1674, both of which may be cannulated to receive the guidewire 112. In some embodiments, the interior of the housing 1672 may define an absorbent member 1676 such as a pad, and a fluid removal member 1678, which may be a rubber seal or other structure designed to slide along the surface of the guidewire 112 and prevent blood from exiting the interior of the housing 1672. In some embodiments, the absorbent member 1676 may be positioned proximate the fluid removal member 1678 so that fluid captured by the fluid removal member 1678 is naturally directed to the absorbent member 1676. In some embodiments, the cap 1674 may optionally be removed before cleaning is carried out.

In some embodiments, the cleaning module 1670 may be advanced away from the distal connector 136 of the system 1600, and may initially interface with the distal connector 136, which may be a blunt cannula or the like. FIG. 16B shows how this interfacing may occur, according to some embodiments.

In some embodiments, retraction of the guidewire 112 and cleaning of the guidewire 112 may be performed together; these two steps need not be mutually exclusive. Specifically, rather than advancing the cleaning module 1670 away from the distal connector 136, the cleaning module 1670 may initially be positioned close to the distal connector 136, and the guidewire 112 may be retracted through the cleaning module 1670 to clean the guidewire 112 as it passes through the cleaning module 1670. In some embodiments, the guidewire 112 may be retracted fully through the cleaning module 1670 or may be retracted only until the distal end 152 of the guidewire 112 is within the cleaning module 1670. Then, in some embodiments, the cleaning module 1670 may remain in place on the distal connector 136 and may be disposed of along with the remainder of the system 1600 after use.

Figure 16C:
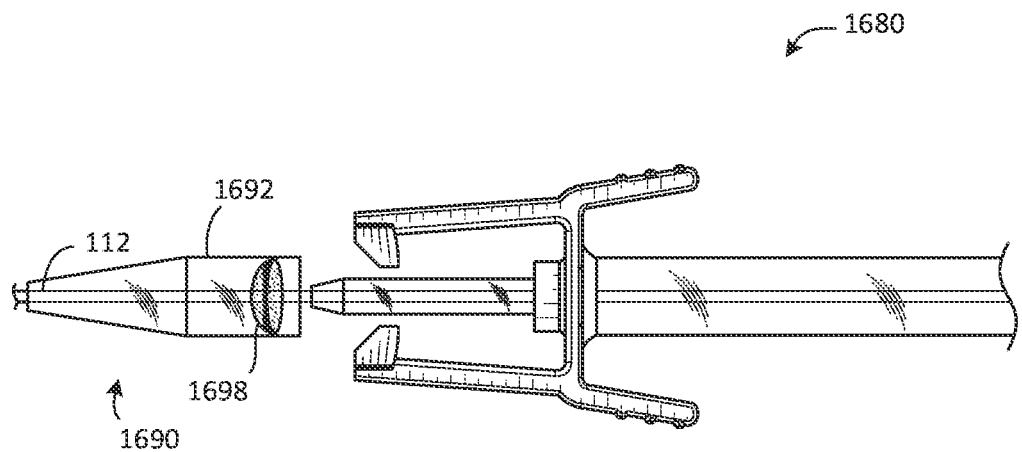
FIG. 16C is a front elevation view of the distal end of a system for accessing a patient's vascular system, according to some embodiments.
Figure 17A:
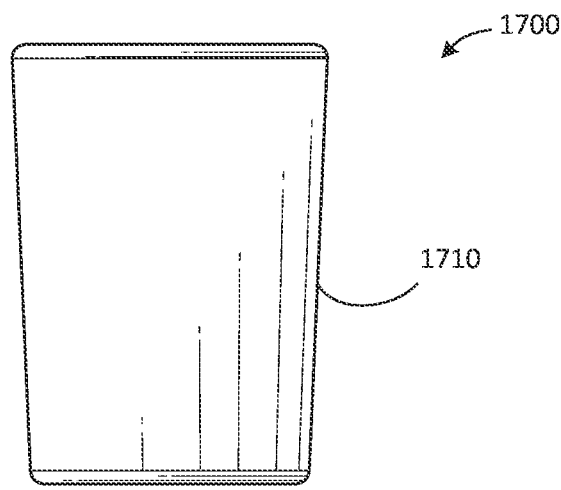
FIGS. 17A, 17B, and 17C are front elevation views of coupling features, according to some embodiments.
Figure 17B:
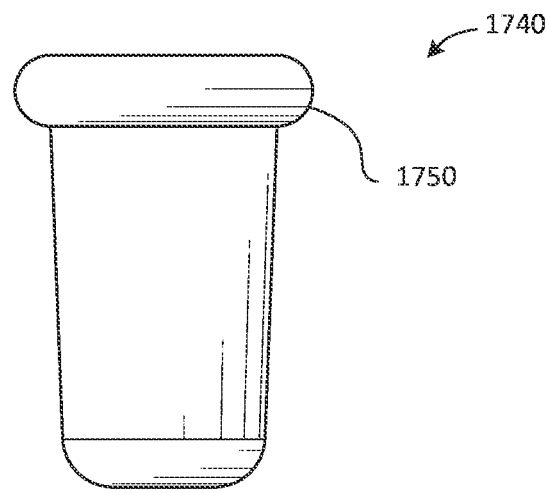
Figure 17C:
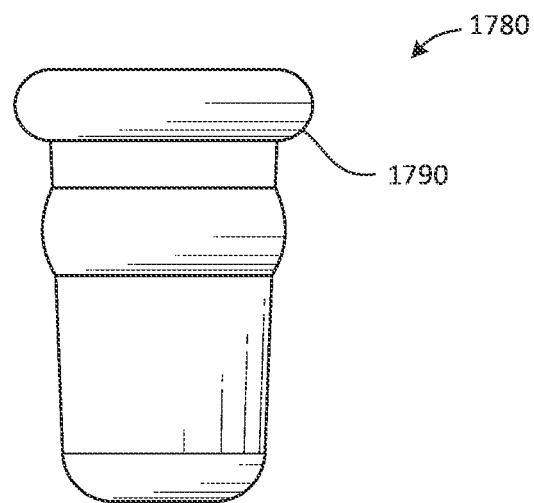
Figure 18A:
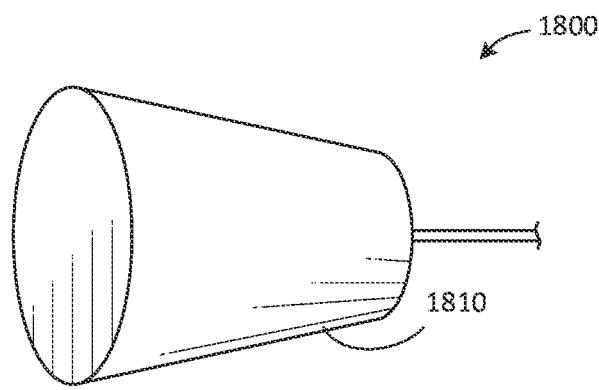
FIGS. 18A, 18B, and 18C are front/side elevation views of coupling features, according to some embodiments.
Figure 18B:
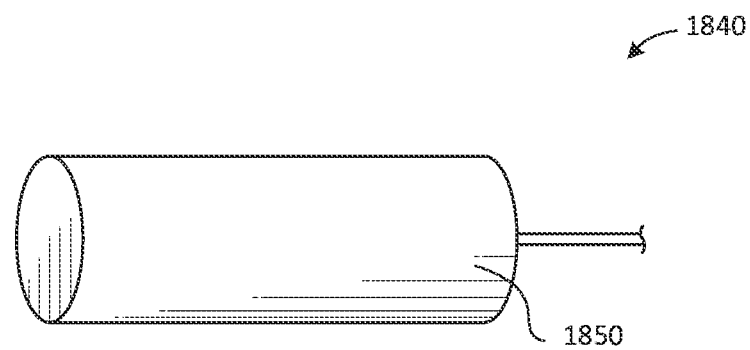
Figure 18C:
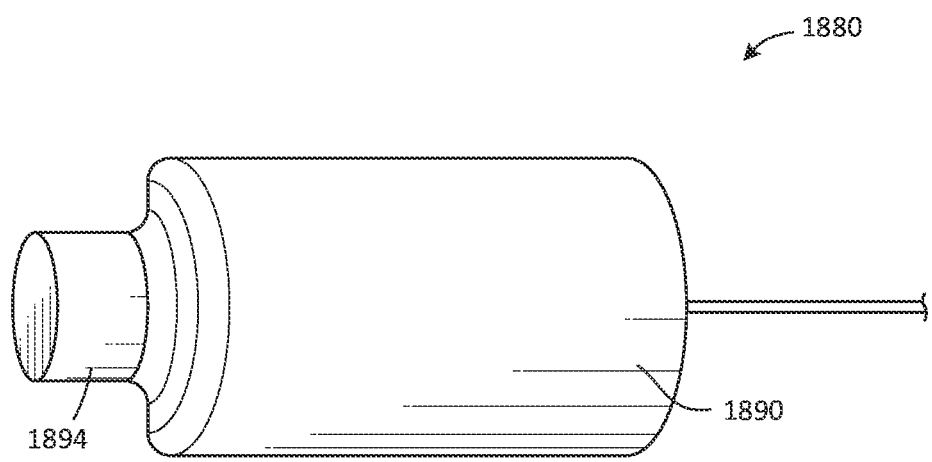

FIG. 16C is a front elevation view of the distal end of a system 1680 for accessing a patient's vascular system, according to some embodiments. In some embodiments, as in the system 1600 of FIGS. 16A and 16B, the system 1680 may have a cleaning module 1690 that cleans the guidewire 112 in addition to or in the alternative to retracting the guidewire 112 and/or covering the guidewire 112 after use. In some embodiments, the cleaning module 1690 may have a housing 1692 and a fluid removal member 1698, which may use a squeegee effect. In some embodiments, the housing 1692 may be part of a Luer on the proximal end of a VAD, or may be a separate component connected to the proximal end of a VAD.

As mentioned previously, in some embodiments, a coupling feature may serve multiple functions. In some embodiments, the coupling feature is coupled to a retraction mechanism. In some embodiments, the coupling feature receives fluid pressure and causes the guidewire to move in response to the fluid pressure. In some embodiments, the coupling feature may serve as a motion stop to limit deployment and/or retraction of the guidewire. A wide variety of coupling features may be used in conjunction with the present disclosure.

According to various embodiments, a coupling feature may have a tapered exterior or one or more rounded ridges to improve ability to round corners while it is deployed, or flushed into place. In some embodiments, the coupling feature may have fins to help it travel down the tubing. In some embodiments, the coupling feature may have fenestrations in it to allow fluid to flow around it. In some embodiments, the coupling feature may be attached to a guidewire and/or tubing by an interference fit, adhesive, or both. In some embodiments, tapered tubing may also be used so that the large outer diameter end serves as its own coupling feature. In some embodiments, the coupling feature may be colored to increase visibility. In some embodiments, longitudinal ribs can be molded on the outer surface of the coupling feature to keep the coupling feature oriented properly (i.e. parallel to the tube 110) so that the coupling feature will move straight forward during deployment. Alternatively, in some embodiments, the longitudinal ribs can have opposing features to prevent the coupling feature from rotating.

Referring now to FIG. 17, FIGS. 17A, 17B, and 17C are front elevation views of a coupling feature 1700, a coupling feature 1740, and a coupling feature 1780, respectively, according to some embodiments. As illustrated, in some embodiments, the coupling feature 1700 may have a simple "wedge" shape with a frustoconical surface 1710. In some embodiments, the coupling feature 1740 may also have a wedge shape, with a proximal ridge 1750 that interfaces with the interior of the tube 110 to form a seal. In some embodiments, the coupling feature 1780 may have a wedge shape with a pair of ridges 1790 to facilitate retention of a spring or other component of a retraction mechanism.

Referring now to FIG. 18, FIGS. 18A, 18B, and 18C are front/side elevation views of a coupling feature 1800, a coupling feature 1840, and a coupling feature 1880, respectively, according to some embodiments. As illustrated, in some embodiments, the coupling feature 1800 may have a wedge shape similar to that of the coupling feature 1700, with a frustoconical surface 1810 with more dramatic diametral taper. In some embodiments, the coupling feature 1840 may be generally cylindrical in shape, with a cylindrical surface 1850. In some embodiments, the coupling feature 1880 may have a stepped cylindrical shape, with a first cylindrical surface 1890 having a first diameter, and a second cylindrical surface 1894 having a second, smaller diameter.

Figure 19A:
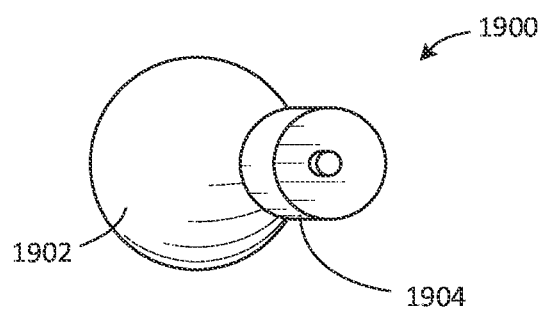
FIGS. 19A, and 19B are front/side elevation views of coupling features, according to some embodiments.
Figure 19B:
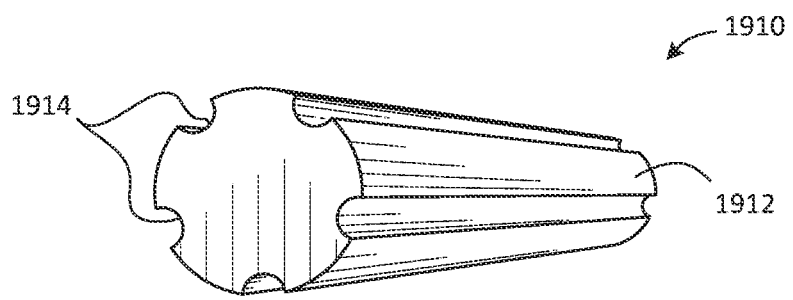

Referring now to FIG. 19, FIGS. 19A, and 19B are front/side elevation views of a coupling feature 1900 and a coupling feature 1910, respectively, according to some embodiments. In some embodiments, the coupling feature 1900 may have a generally spherical surface 1902 with a boss 1904 for connection to the remainder of a guidewire, or to another element. In some embodiments, the coupling feature 1910 may have a splined surface 1912 with grooves 1914 that permit fluid to pass around the coupling feature 1910 (for example, between the coupling feature 1910 and the interior wall of the tube 110).

Figure 19C:
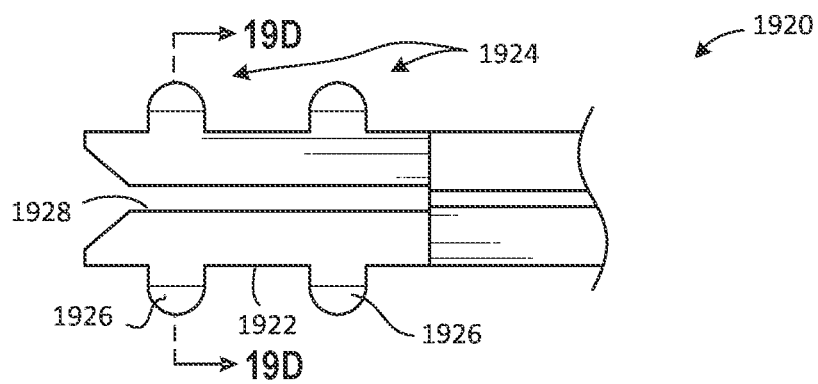
FIGS. 19C and 19D are front elevation and side elevation views, respectively, of the distal end of a coupling feature, according to some embodiments.
Figure 19D:
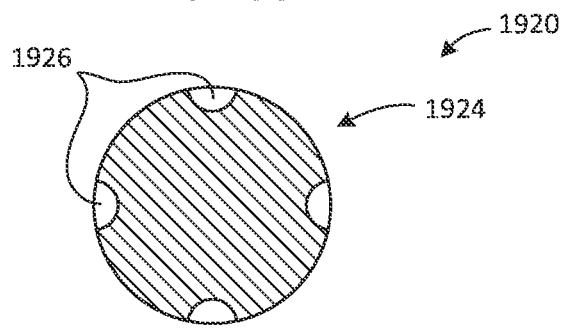

FIGS. 19C and 19D are front elevation and side elevation views, respectively, of the distal end of a coupling feature 1920, according to some embodiments. As illustrated, in some embodiments, the coupling feature 1920 may have a generally cylindrical surface 1922 with two ridges 1924 that protrude outward to engage the interior surface of the tube 110. In some embodiments, each of the ridges 1924 may have notches 1926 spaced about its periphery to permit fluid to flow between the ridges 1924 and the interior surface of the tube 110. In some embodiments, the coupling feature 1920 may further have a bore 1928 through which fluid can flow, for example, for infusing fluid into the patient's vascular system, or for aspirating blood from the vascular system.

Figure 19E:
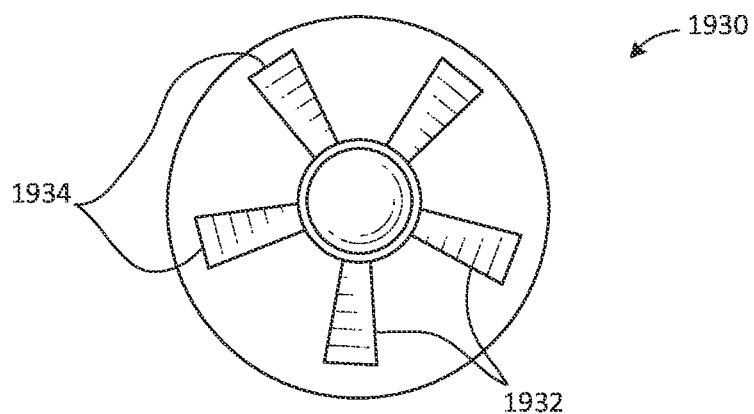
FIGS. 19E and 19F are side elevation and front elevation views, respectively, of a coupling feature, according to some embodiments.
Figure 19F:
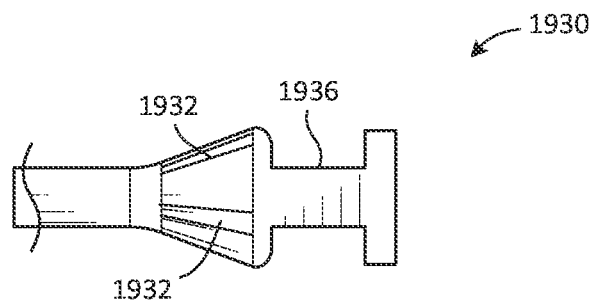

FIGS. 19E and 19F are side elevation and front elevation views, respectively, of a coupling feature 1930, according to some embodiments. As illustrated, in some embodiments, the coupling feature 1930 may have a set of splines 1932 defining a generally frustoconical exterior surface 1934, adjoining a smaller cylindrical section 1936. In some embodiments, the splines 1932 may help maintain the coupling feature 1930 properly oriented within the tube 110, and also facilitate fluid flowing around the coupling feature 1930.

Figure 19G:
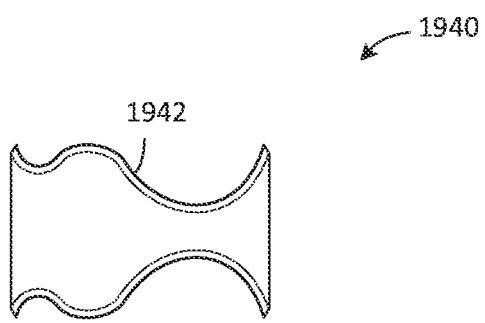
FIG. 19G is a side elevation view of a coupling, according to some embodiments.
Figure 20A:
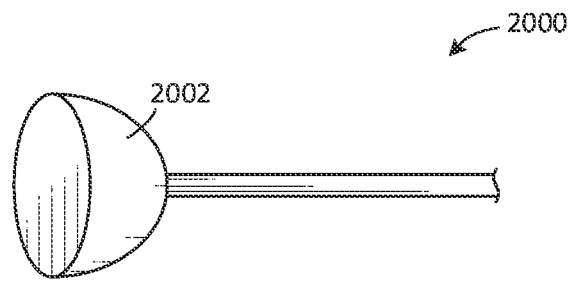
FIGS. 20A, 20B, 20C, and 20D are front/side elevation views of coupling features, according to some embodiments.
Figure 20B:
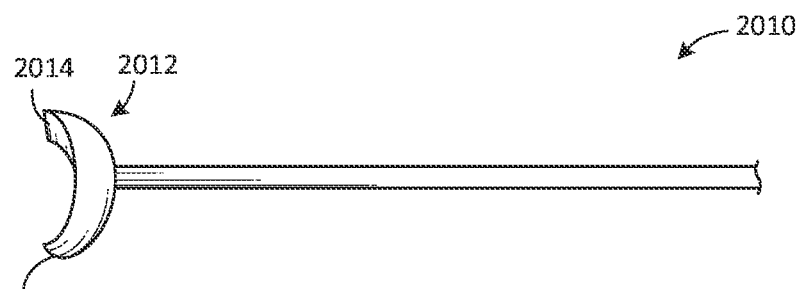
Figure 20C:
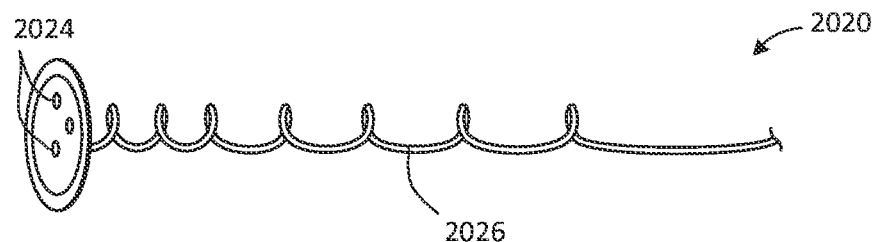
Figure 20D:
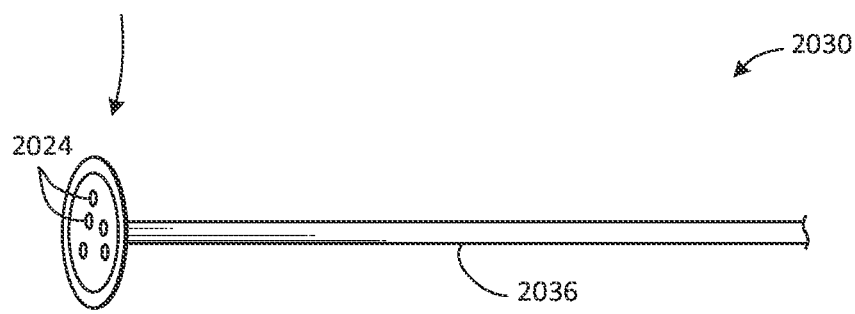

FIG. 19G is a side elevation view of a coupling feature 1940, according to some embodiments. In some embodiments, the coupling feature 1940 may have a more organic shape, defining a complex surface 1942. In some embodiments, the complex surface 1942 may optionally include spline as in other embodiments.

Referring now to FIG. 20, FIGS. 20A, 20B, 20C, and 20D are front/side elevation views of a coupling feature 2000, a coupling feature 2010, a coupling feature 2020, and a coupling feature 2030, according to some embodiments. In some embodiments, the coupling feature 2000 has a generally parabolic surface 2002, while the coupling feature 2010 has a crescent-shaped member 2012 that is not axi-symmetrical, and engages the interior surfaces of the tube 110 with tips 2014 of the crescent-shaped member 2012. In some embodiments, the coupling feature 2020 and the coupling feature 2030 both have a disc-shaped member 2022 with holes 2024 that permit fluid to flow through the disc-shaped member 2022. In some embodiments, the coupling feature 2020 is secured to a helical guide wire portion 2026, while the coupling feature 2030 is secured to a straight guide wire portion 2036.

Figure 21:
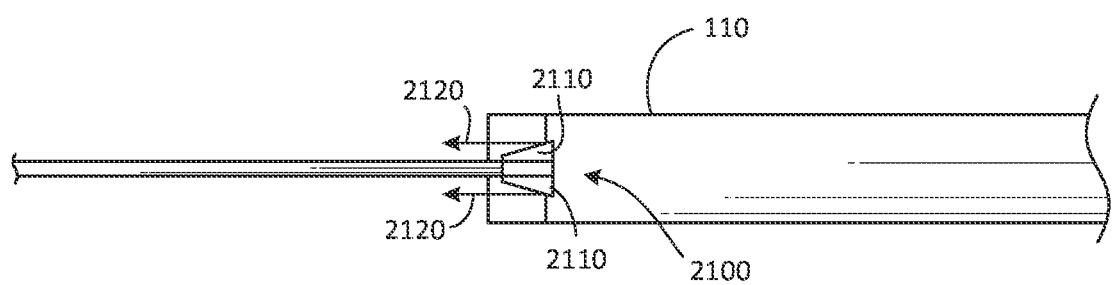
FIG. 21 is a front elevation view of a coupling feature, according to some embodiments.

Referring now to FIG. 21, FIG. 21 is a front elevation view of a coupling feature 2100, according to some embodiments. In some embodiments, the coupling feature 2100 may have wedge shape with splines 2110 that permit fluid to flow through the coupling feature therebetween, in the direction of the arrows 2120.

Figure 22:
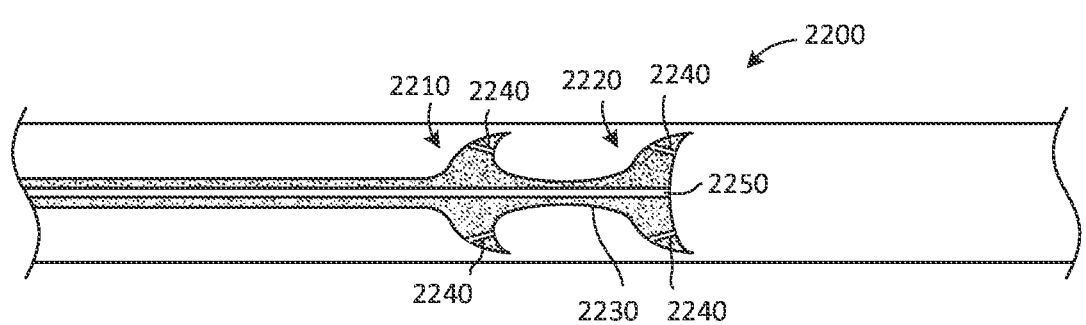
FIG. 22 is a front elevation view of a coupling feature, according to some embodiments.

Referring now to FIG. 22, FIG. 22 is a front elevation view of a coupling feature 2200, according some embodiments. In some embodiments, the coupling feature 2200 may have a first fin 2210 and a second fin 2220, each of which has a crescent-shape. In some embodiments, the first fin 2210 and the second fin 2220 may be separated from each other by a thin, flexible member 2230 that bends to permit some relative rotation between the first fin 2210 and the second fin 2220, thereby accommodating curves in the interior surface of the tube 110. In some embodiments, the crescent-shapes may help provide a seal against the interior wall of the tube 110, and capture hydraulic pressure to provide reliable deployment in response to flushing pressure. In some embodiments, small holes 2240 passing through the first fin 2210 and the second fin 2220 may help provide some lubrication and/or fluid passage therethrough. In some embodiments, an interior bore 2250 may enable aspiration of blood and/or other fluids from the patient's vascular system.

Figure 23:
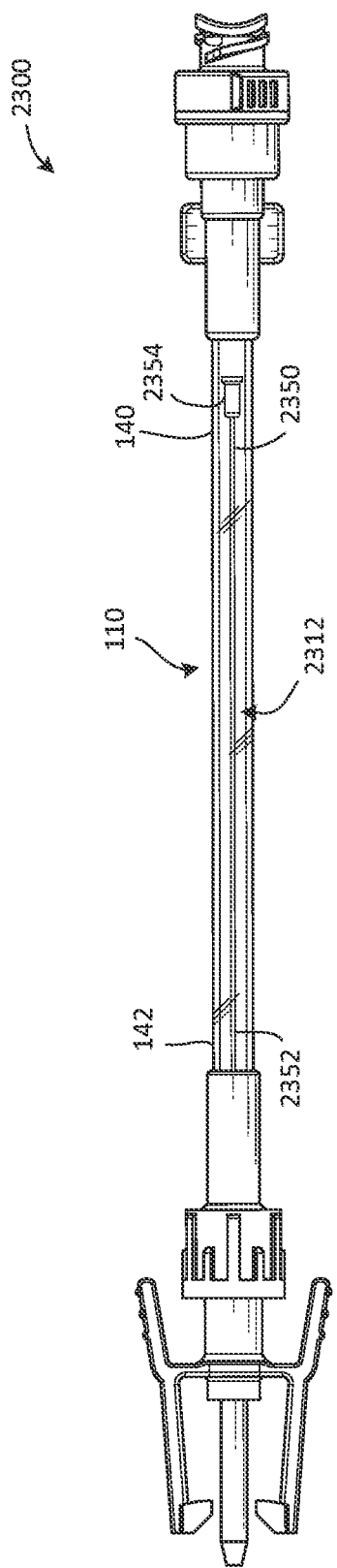
FIG. 23 is a front elevation view of a system for accessing a patient's vascular system, according to some embodiments.

Referring now to FIG. 23, FIG. 23 is a front elevation view of a system 2300 for accessing a patient's vascular system, according to some embodiments. In some embodiments, the system 2300 may have a tube 110 with a proximal end 140 and a distal end 142, and a guidewire 2312 with a proximal end 2350 and a distal end 2352. In some embodiments, a coupling feature 2354 near the proximal end 2350 may couple the guidewire 2312 to a retraction mechanism (not illustrated), such as any of the retraction mechanisms previously described herein. In the alternative, in some embodiments, the system 2300 may not have a retraction mechanism, and may instead function in conjunction with a protective shield and/or a cleaning module as disclosed herein.

Figure 24:
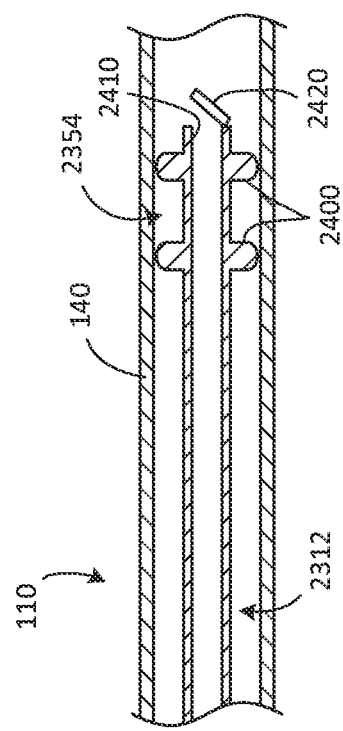
FIG. 24 is a front elevation section view of the coupling feature of the system of FIG. 23, according to some embodiments.

Referring now to FIG. 24, FIG. 24 is a front elevation, section view of the proximal portion of the system 2300 of FIG. 23, according to some embodiments. As illustrated, in some embodiments, the coupling feature 2354 may have two ridges 2400 that extend outward to contact the interior surface of the wall 139 of the tube 110. In some embodiments, the presence of multiple ridges 2400 may help the coupling feature 2354 flex around bends in the tube 110. In some embodiments, the guidewire 2312 may have a bore 2410 extending through its length to permit fluid to be aspirated from the patient's vascular system, through the guidewire 2312. In some embodiments, the coupling feature 2354 may further have a valve 2420 that closes in response to positive pressure proximal to the coupling feature 2354 (as when the guidewire 2312 is to be deployed via flushing), and opens, as illustrated, in response to positive pressure from the vascular system to permit aspiration.

In some embodiments, various catch mechanisms may be used to prevent premature retraction of a guidewire, such as the guidewire 2312 of FIGS. 23 and 24. Various examples will be illustrated and described in connection with FIGS. 25A through 25E.

FIG. 25A is a front elevation section view of the proximal portion of a system 2500 for accessing a patient's vascular system, according to some embodiments. In some embodiments, the system 2500 has the guidewire 2312 of FIGS. 23 and 24, along with a tube 2510 with a modified configuration designed to incorporate a catch to lock the guidewire 2312 in the deployed position until retraction is desired.

Specifically, in some embodiments, the tube 2510 may have a wall 2539 defining an interior surface 2545. In some embodiments, the interior surface 2545 may be shaped to provide a detent 2560 and a locking flap 2570. In some embodiments, the detent 2560 may be sized to receive the adjacent edge of either of the ridges 2400 to provide one or two stable resting positions for the guidewire 2312. In some embodiments, the locking flap 2570 may lie flat against the remainder of the interior surface 2545 as the coupling feature 2354 is moving distally through the tube 2510, but may be biased to pivot into the interior of the tube 2510 after one of the ridges 2400 has passed beyond it. Thus, in some embodiments, the locking flap 2570 may prevent proximal motion of the guidewire 2312 until desired by the user.

In some embodiments, the restraining force of the locking flap 2570 may be overcome by applying sufficient force, urging the guidewire 2312 to move proximally, to bend the locking flap 2570 back proximally. Then, one or both of the ridges 2400 may be able to pass proximally back over the locking flap 2570. In alternative embodiments, a user-actuated release mechanism may be connected to the locking flap 2570 to enable the user to disengage the locking flap 2570, to facilitate retraction of the guidewire 2312.

FIGS. 25B and 25C are front elevation views of a proximal portion of a system 2580 for accessing a patient's vascular system, according to some embodiments, with the guidewire 2312 in unlocked and locked positions, respectively. In some embodiments, the system 2580 also includes the guidewire 2312 of FIGS. 23 and 24 and has a tube 2582 with a modified configuration. In some embodiments, the tube 2582 has a wall 2584 with an interior surface 2586.

In some embodiments, the interior surface 2586 defines a detent 2587, which may have an annular configuration, and a locking flap 2588. In some embodiments, the detent 2587 and the locking flap 2588 may function in substantially the same manner as their counterparts of the system 2500 of FIG. 25A. However, in some embodiments, the detent 2587 may be larger and may extend full circle around the coupling feature 2354, providing more secure fixation. Additionally, in some embodiments, the interior surface 2586 of the wall 2584 of the tube 2582 may also define a reduced-diameter portion 2589 of the tube, proximal to the detent 2587, where the tube 2582 is too narrow to receive the coupling feature 2354. This may provide an additional hard stop to limit proximal travel of the guidewire 2312.

FIGS. 25D and 25E are front elevation views of a proximal portion of a system 2590 for accessing a patient's vascular system, according to some embodiments, with a guidewire 2512 in unlocked and locked positions, respectively. In some embodiments, the guidewire 2512 may be similar to the guidewire 2312 of FIGS. 23 and 24. In some embodiments, the system 2590 may further have a tube 2592 with a modified configuration. In some embodiments, the tube 2592 has a wall 2594 with an interior surface 2596.

In some embodiments, the interior surface 2596 defines a detent 2597, which may have an annular configuration. However, in some embodiments, the interior surface 2596 may not define a locking flap. Rather, in some embodiments, a locking flap 2598 may be positioned on a coupling feature 2554 of the guidewire 2512. Rather than locking with the ridges 2400 of the coupling feature 2554, in some embodiments the locking flap 2598 may lock with the detent 2597, as illustrated in FIG. 25E. In some embodiments, the interior surface 2596 of the wall 2594 of the tube 2592 may also define a reduced-diameter portion 2599 of the tube, proximal to the detent 2597, where the tube 2592 is too narrow to receive the coupling feature 2554.

The various systems of the present disclosure may be inserted through various VAD's, including but not limited to straight and integrated catheters. Infusion, blood draw, or other vascular access may occur through the system itself, an integrated PIVC extension set, an extension set off the blunt cannula device, or a separate extension set such as a T connector.

Figure 26A:
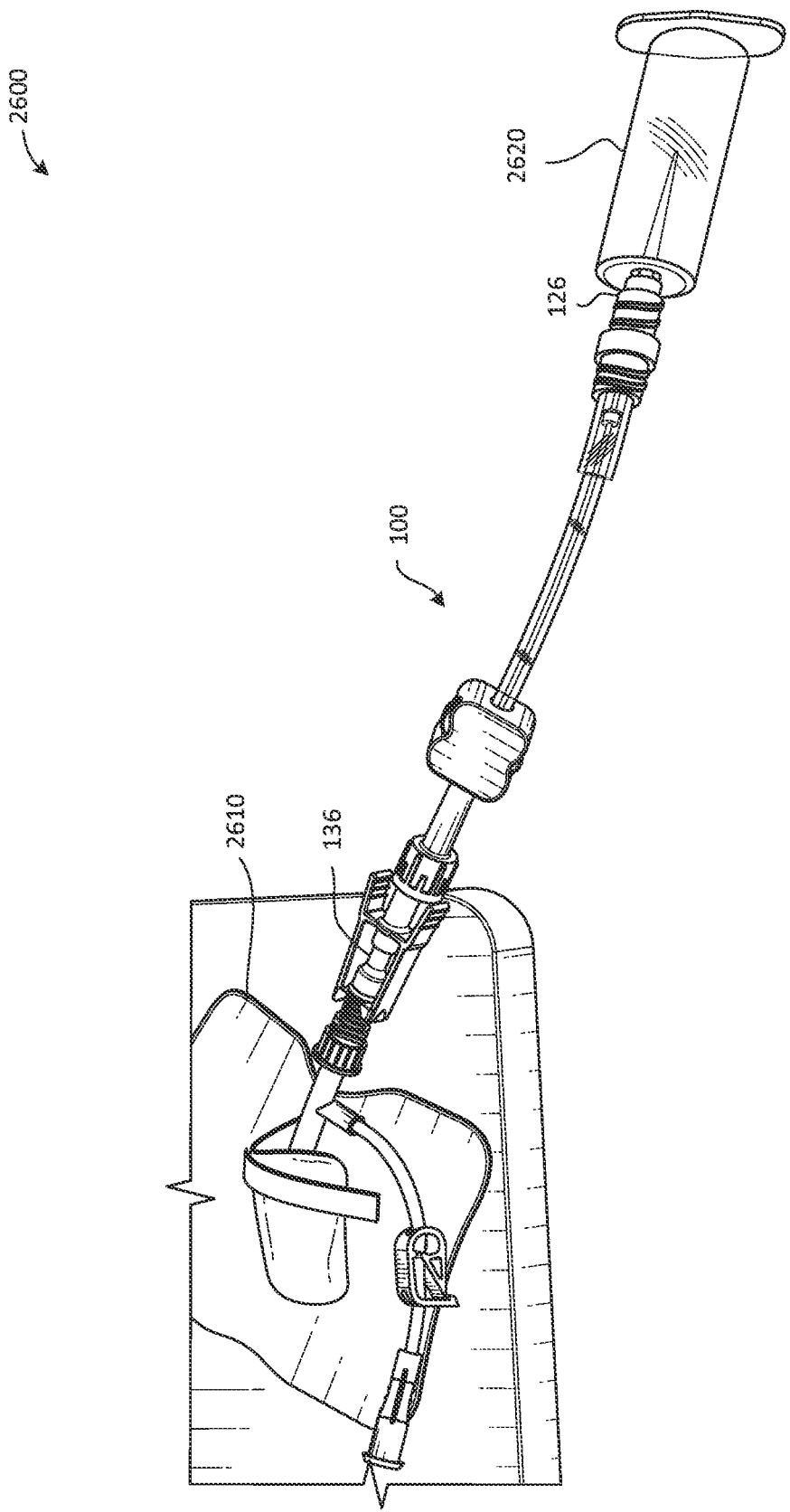
FIGS. 26A and 26B are perspective views of assemblies that include the system of FIG. 1, according to some embodiments.
Figure 26B:
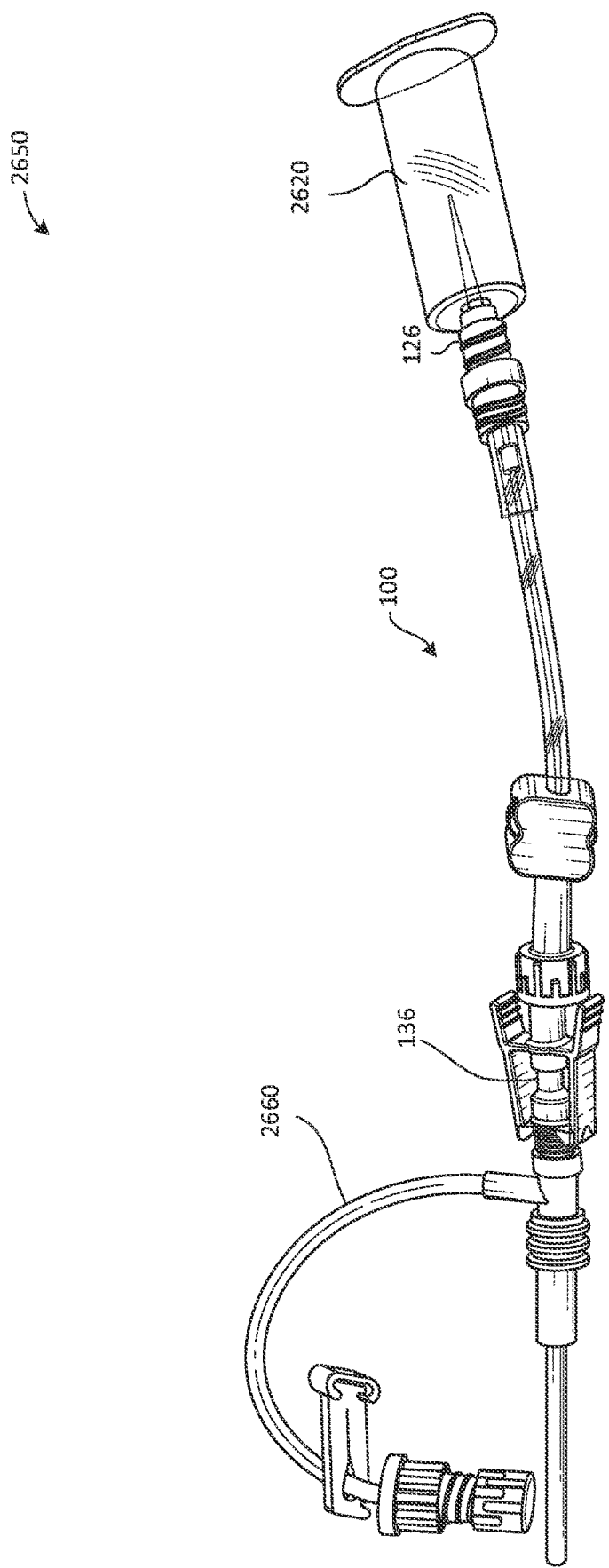
Figure 27A:
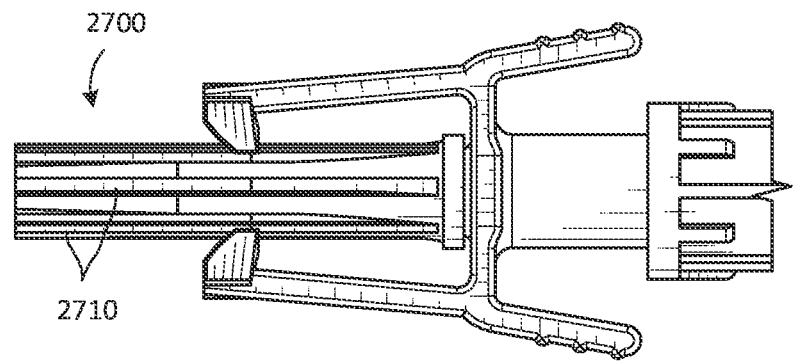
FIGS. 27A, 27B, and 27C are front elevation, front elevation section, and front elevation section views, respectively, of caps, according to some embodiments.
Figure 27B:
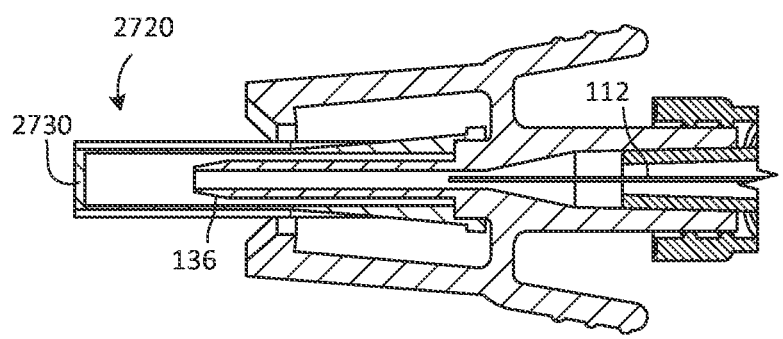
Figure 27C:
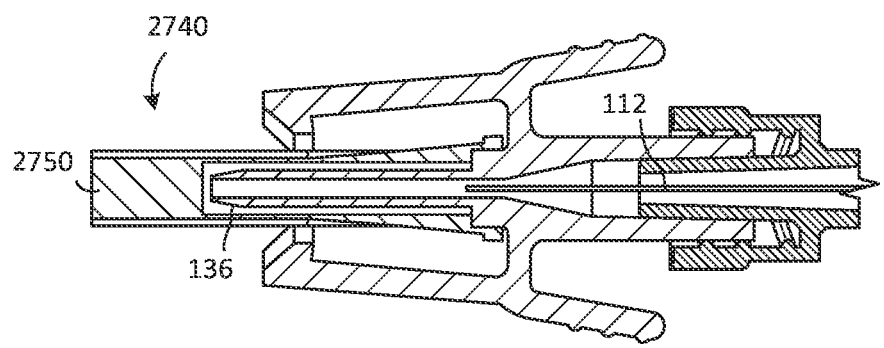

Referring now to FIG. 26, FIGS. 26A and 26B are perspective views of assemblies 2600, 2650 that include the system 100 of FIG. 1, according to some embodiments. More particularly, FIG. 26A illustrates an assembly 2600 with the system 100, a first VAD 2610 coupled to the distal connector 136 of the system 100, and a syringe 2620 coupled to the proximal connector 126 of the system 100. FIG. 26B illustrates an assembly 2650 with the system 100 a second VAD 2660, configured differently from the first VAD 2610, coupled to the distal connector 136 of the system 100, and a syringe 2620 coupled to the proximal connector 126 of the system 100. Although the system 100 is illustrated in FIGS. 26A and 26B, in some embodiments, any other system disclosed herein may be used in conjunction with the first VAD 2610, the second VAD 2660, the syringe 2620, or any other VAD or pressurized fluid source known in the art.

Referring now to FIG. 27, FIGS. 27A, 27B, and 27C are front elevation, front elevation section, and front elevation section views, respectively, of a cap 2700, a cap 2720, and a cap 2740, according to some embodiments. In some embodiments, the cap 2700, the cap 2720, and the cap 2740, are illustrated on the system 100 of FIG. 1, but may be used in connection with any other system disclosed herein.

In some embodiments, the cap 2700 may have ridges 2710 that serve as grip features to facilitate removal of the cap 2700 from the distal connector 136. In some embodiments, the cap 2720 and the cap 2740 may have solid distal ends 2730 and 2750, respectively, that keep the distal end 152 of the guidewire 112 from siding proximally out of the cap 2720 or the cap 2740 during shipping and priming. In alternative embodiments, a cap may have other features such as vents in the side walls or the distal wall.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A system for accessing a patient's vascular system, the system comprising:
    a tube comprising a wall that defines an exterior surface and a lumen with a proximal end and a distal end, wherein the proximal end is connectable to a source of pressurized fluid;
    a guidewire that is deployable by sliding distally from a retracted position in which the guidewire resides in the lumen, to a deployed position in which the guidewire extends beyond the distal end, wherein the guidewire is deployable in response to pressure, proximal to the lumen, from the source of pressurized fluid; and
    at least one element selected from the group consisting of:
        a retraction mechanism that can be actuated to retract the guidewire from the deployed position to the retracted position; and
        a protective shield that can be actuated to extend distally from the distal end of the tube to cover the guidewire in the deployed position.

2. The system of claim 1, wherein:
the system comprises an extension set for a vascular access device (VAD); and
the distal end comprises a blunt cannula configured to mate with a needleless access connector of the VAD.

3. The system of claim 2, further comprising a cap configured to cover the blunt cannula prior to attachment of the blunt cannula to the VAD.

4. The system of claim 1, wherein:
the element comprises the retraction mechanism; and
the retraction mechanism is slidably coupled to the exterior surface and is coupled to the guidewire such that motion of the retraction mechanism toward the proximal end retracts the guidewire from the deployed position to the retracted position.

5. The system of claim 1, wherein:
the element comprises the retraction mechanism;
the guidewire comprises:
  a distal portion with an elongated shape; and
  a proximal portion with a coupling feature with a cross-sectional shape that is enlarged relative to the distal portion; and
the retraction mechanism is coupled to the coupling feature through the wall.

6. The system of claim 5, wherein the coupling feature comprises at least one selection from the group consisting of:
a wedge shape;
one or more rounded ridges;
one or more fins;
one or more splines;
one or more longitudinal ribs; and
one or more anti-rotation features.

7. The system of claim 5, wherein the retraction mechanism compresses the wall into contact with the coupling feature to cause the wall to urge the coupling feature to move proximally in response to proximal motion of the retraction mechanism.

8. The system of claim 7, wherein the retraction mechanism comprises at least one selection from the group consisting of:
one or more wheels that engage the exterior surface to compress the tube;
one or more ball bearings that engage the exterior surface to compress the tube; and
one or more manually compressible walls that can be flexed toward the tube.

9. The system of claim 5, wherein:
the element comprises the retraction mechanism; and
the retraction mechanism comprises at least one selection from the group consisting of:
  one or more magnets that magnetically engage the coupling feature;
  one or more springs coupled to the coupling feature; and
  a tether secured to the coupling feature.

10. The system of claim 1, further comprising a spring that urges the guidewire to deploy from the retracted position to the deployed position.

11. The system of claim 1, wherein:
the element comprises the protective shield; and
the system further comprises an absorbent component positioned to remove blood from the guidewire after deployment of the guidewire.

12. The system of claim 1, wherein the guidewire comprises at least one selection from the group consisting of:
a spring comprising a variable pitch; and
a secondary tube comprising an interior bore through which blood can be aspirated from the vascular system.

13. The system of claim 12, wherein:
the proximal end is connectable to a source of pressurized fluid;
the guidewire is deployable in response to pressure, proximal to the lumen, from the source of pressurized fluid;
the guidewire comprises the secondary tube; and
the guidewire further comprises a valve that is closed during deployment of the guidewire and open during aspiration of blood from the vascular system.

14. The system of claim 13, wherein at least one of the guidewire and the tube further comprises a catch mechanism that retains the guidewire in the deployed position.

15. A method for accessing a patient's vascular system, the method comprising:
positioning a tube proximate the vascular system, the tube comprising an exterior surface and a lumen with a proximal end and a distal end;
connecting the proximal end to a source of pressurized fluid;
dispensing pressurized fluid from the source to deploy a guidewire by sliding the guidewire distally, from a retracted position in which the guidewire resides in the lumen, to a deployed position in which the guidewire extends beyond the distal end; and
performing at least one step selected from the group consisting of:
  retracting the guidewire from the deployed position to the retracted position by sliding a retraction mechanism, slidably coupled to the exterior surface, proximally; and
  actuating a protective shield to extend distally from the distal end of the tube to cover the guidewire in the deployed position.

16. The method of claim 15, wherein:
the step comprises retracting the guidewire by sliding the retraction mechanism; and
the method further comprises, prior to deploying the guidewire, moving the retraction mechanism to a predetermined position such that, during deployment of the guidewire, the retraction mechanism limits a range of proximal motion of the guidewire.

17. The method of claim 15, wherein:
the step comprises actuating the protective shield; and
the method further comprises, with an absorbent component, removing blood from the guidewire after deployment of the guidewire.

18. The method of claim 15, wherein:
the guidewire comprises:
  a secondary tube comprising an interior bore; and
  a valve;
wherein deploying the guidewire comprises dispensing pressurized fluid from the source with the valve closed to prevent fluid flow through the interior bore; and
the method further comprises, after deploying the guidewire:
  opening the valve to permit fluid flow through the interior bore; and
  aspirating blood through the interior bore.

19. A system for accessing a patient's vascular system, the system comprising:
a tube comprising a wall that defines an exterior surface and a lumen with a proximal end and a distal end;
a guidewire that is deployable by sliding distally from a retracted position in which the guidewire resides in the lumen, to a deployed position in which the guidewire extends beyond the distal end, the guidewire comprising:
  a distal portion with an elongated shape; and
  a proximal portion with a coupling feature with a cross-sectional shape that is enlarged relative to the distal portion; and
a retraction mechanism that can be actuated to retract the guidewire from the deployed position to the retracted position;
wherein:
  the proximal end is connectable to a source of pressurized fluid;
  the guidewire is deployable in response to pressure, proximal to the lumen, from the source of pressurized fluid;
  the system comprises an extension set for a vascular access device (VAD); and
  the distal end comprises a blunt cannula configured to mate with a needleless access connector of the VAD.

* * * * *